(12) United States Patent
Matsuura

(10) Patent No.: US 9,682,213 B2
(45) Date of Patent: Jun. 20, 2017

(54) INSERTION PORTION RIGIDITY CHANGEABLE CATHETER AND OPERATION METHOD OF ENDOSCOPE SYSTEM

(71) Applicant: OLYMPUS CORPORATION, Tokyo (JP)

(72) Inventor: Wataru Matsuura, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 248 days.

(21) Appl. No.: 14/491,533

(22) Filed: Sep. 19, 2014

(65) Prior Publication Data

US 2015/0011933 A1    Jan. 8, 2015

Related U.S. Application Data

(63) Continuation of application No. 13/495,076, filed on Jun. 13, 2012, now abandoned, which is a
(Continued)

(30) Foreign Application Priority Data

Nov. 25, 2010  (JP) .................................. 2010-262755

(51) Int. Cl.
*A61M 29/00* (2006.01)
*A61M 25/00* (2006.01)
(Continued)

(52) U.S. Cl.
CPC ..... *A61M 25/0052* (2013.01); *A61B 1/00082* (2013.01); *A61B 1/00119* (2013.01);
(Continued)

(58) Field of Classification Search
CPC ............ A61M 25/008; A61M 25/1002; A61M 2025/0063; A61B 1/00082; A61B 1/00119; A61B 1/0125; A61B 1/015
See application file for complete search history.

(56) References Cited

U.S. PATENT DOCUMENTS 4,329,980 A  *  5/1982  Terada ............... A61B 1/00078
                                                  600/140
4,413,989 A    11/1983  Schjeldahl et al.
(Continued)

FOREIGN PATENT DOCUMENTS

GB          2045964 A      11/1980
JP          6137931 B2     8/1986
(Continued)

OTHER PUBLICATIONS

International Search Report mailed Feb. 21, 2012 issued in International Application No. PCT/JP2011/076906.
(Continued)

*Primary Examiner* — Richard Louis
(74) *Attorney, Agent, or Firm* — Scully, Scott, Murphy & Presser, PC

(57) ABSTRACT

An insertion portion rigidity changeable catheter with a balloon has an insertion portion including a coil-shaped member which is extensible and contractible, with a compression length set to be a predetermined length, and a sheath which is a tube body with flexibility having a fluid conduit, includes a sheath main body surrounded by the coil-shaped member, and a sheath end portion provided at one end side of the sheath main body, and having a contact surface which one end surface of the coil-shaped member contacts, has one opening of the fluid conduit in the sheath end portion and has another opening of the fluid conduit at another end side of the sheath main body, an inflatable/
(Continued)

deflatable balloon which is inflated by being supplied with a fluid via the one opening of the fluid conduit to expand to a diameter larger than an outside diameter of the sheath end portion, and is deflated by the fluid being discharged via the one opening to be brought into close contact with an outer circumferential face of the sheath end portion, and an operation section which is fixedly provided at another end side of the sheath, and includes an operation section main body including a fluid supply and discharge apparatus connection portion which is directly or indirectly connected to a fluid supply and discharge apparatus which performs supply of the fluid into the balloon via the fluid conduit, or discharge, and a slide member which is slidably disposed in an inner surface side of the operation section main body, and is disposed at another end side of the operation section main body by an elastic force of the coil-shaped member, wherein the fluid supply and discharge apparatus connection portion is fixed to the operation section main body, and the slide member is provided to freely advance and retract with respect to the fluid supply and discharge apparatus connection portion.

2 Claims, 20 Drawing Sheets

Related U.S. Application Data continuation of application No. PCT/JP2011/076906, filed on Nov. 22, 2011.

(51) Int. Cl.
*A61B 1/00* (2006.01)
*A61B 1/012* (2006.01)
*A61B 1/015* (2006.01)
*A61M 25/10* (2013.01)

(52) U.S. Cl.
CPC .......... *A61B 1/015* (2013.01); *A61B 1/0125* (2013.01); *A61M 25/008* (2013.01); *A61M 25/1002* (2013.01); *A61M 2025/0063* (2013.01)

(56) References Cited

U.S. PATENT DOCUMENTS

| | | | |
|---|---|---|---|
| 4,649,922 A | | 3/1987 | Wiktor |
| 4,813,934 A | | 3/1989 | Engelson et al. |
| 4,927,412 A | | 5/1990 | Menasche |
| 4,946,466 A | * | 8/1990 | Pinchuk ............... A61M 25/09 604/913 |
| 5,573,508 A | * | 11/1996 | Thornton ............ A61M 25/104 604/102.02 |
| 5,826,588 A | | 10/1998 | Forman |
| 5,885,208 A | | 3/1999 | Moriyama |
| 5,911,717 A | | 6/1999 | Jacobsen et al. |
| 6,013,054 A | | 1/2000 | Jiun Yan |
| 6,203,494 B1 | | 3/2001 | Moriyama |
| 2004/0002749 A1 | | 1/2004 | Joye et al. |
| 2005/0288551 A1 | | 12/2005 | Callister et al. |
| 2006/0079926 A1 | | 4/2006 | Desai et al. |
| 2006/0217653 A1 | | 9/2006 | Doty |
| 2009/0062871 A1 | | 3/2009 | Chin et al. |
| 2009/0082723 A1 | | 3/2009 | Krogh et al. |
| 2009/0171427 A1 | | 7/2009 | Melsheimer et al. |

FOREIGN PATENT DOCUMENTS

| | | |
|---|---|---|
| JP | 2002-360505 A | 12/2002 |
| JP | 2005334474 | 12/2005 |
| JP | 2007-054217 A | 3/2007 |
| JP | 2007319668 A | 12/2007 |
| JP | 2009515617 A | 4/2009 |
| JP | 2010537736 A | 12/2010 |
| WO | 2007057132 A1 | 5/2007 |
| WO | 2009029639 A1 | 3/2009 |

OTHER PUBLICATIONS

Non-Final US Office Action dated Jul. 25, 2013 issued in U.S. Appl. No. 13/495,076.
Extended Supplementary European Search Report dated Apr. 3, 2014 issued in Application No. / Patent No. 11843134.5-1160 / 2574269 PCT/JP2011076906.
Final US Office Action dated Mar. 19, 2014 issued in U.S. Appl. No. 13/495,076.

* cited by examiner

US 9,682,213 B2

INSERTION PORTION RIGIDITY CHANGEABLE CATHETER AND OPERATION METHOD OF ENDOSCOPE SYSTEM

CROSS REFERENCE TO RELATED APPLICATION

This application is a continuation application of U.S. patent application Ser. No. 13/495,076, filed Jun. 13, 2012, which is a continuation application of PCT International Application No. PCT/JP2011/076906, filed on Nov. 22, 2011, and claims benefit of Japanese Application No. 2010-262755 filed in Japan on Nov. 25, 2010, the entire contents of each of which are incorporated herein by this reference.

BACKGROUND OF THE INVENTION

1. Field of the Invention

The present invention relates to an insertion portion rigidity changeable catheter with a balloon which guides an insertion portion of an endoscope to a target site.

2. Description of the Related Art

In endoscopes for medical use, an endoscope which is inserted into tube cavities such as a gaster, and intestines has an elongated insertion portion. A tube cavity is in a shape which is curved stereoscopically and complicatedly. A bending portion which can change an orientation of an insertion portion distal end portion in, for example, a vertical direction, a lateral direction and the like is provided at a distal end side of the insertion portion of the endoscope. The bending portion performs bending motion in a desired direction by a surgeon operating, for example, a bending lever which is provided at an operation section which the surgeon grasps.

For example, in manipulation of inserting an insertion portion with a small diameter including a bending portion into a biliary tract, the surgeon inserts the insertion portion distal end portion of an endoscope to a vicinity of a biliary tract first. Thereafter, the surgeon performs a catheter introducing manipulation, a catheter fixing manipulation and an insertion portion introducing manipulation. The catheter introducing manipulation is the manipulation of introducing a catheter with a balloon into a biliary tract via the treatment instrument channel of an endoscope. The catheter fixing manipulation is a manipulation of fixing the balloon of a catheter with the balloon to a biliary tract. The insertion portion introducing manipulation is a manipulation of inserting an insertion portion into a biliary tract along the catheter with a balloon fixed into the biliary tract.

Here, the catheter introducing manipulation, the catheter fixing manipulation and the insertion portion introducing manipulation will be described.

First, the surgeon introduces an insertion portion 100 into a duodenum 110, and disposes the insertion portion 100 in the vicinity of a biliary tract as shown in FIG. 1. Next, the surgeon performs an operation of bending a bending portion 102 to cause a distal end face of a distal end portion 101 to face a tract outlet (hereinafter, described as an outlet) which is a duodenum side opening of a biliary tract 111. Thereafter, the surgeon performs the catheter introducing manipulation, the catheter fixing manipulation and the insertion portion introducing manipulation.

The catheter introducing manipulation will be described.

The surgeon leads a catheter 120 with a balloon from an opening of a treatment instrument channel (not illustrated) included in a front end face of the distal end portion 101. Subsequently, the surgeon disposes a treatment instrument distal end portion 121 in the vicinity of the outlet 112 of the biliary tract 111.

Next, the surgeon inserts a treatment instrument insertion portion 122 of the catheter 120 with a balloon into the biliary tract 111 by a predetermined amount from a distal end face of the insertion portion 100. As a result, the treatment instrument distal end portion 121 is disposed at a desired position inside the biliary tract 111.

The catheter fixing manipulation will be described.

After the surgeon disposes the treatment instrument distal end portion 121 at the aforementioned position in the biliary tract 111, the surgeon supplies, for example, air to a balloon 123 which is provided at the treatment instrument distal end portion 121. The balloon 123 inflates as shown by the broken line of FIG. 2, and the inflated balloon 123 is brought into close contact with an inner wall of the biliary tract 111. As a result, the treatment instrument distal end portion 121 of the catheter 120 with the balloon is fixed to a desired position in the biliary tract 111.

The insertion portion introducing manipulation will be described.

After the surgeon fixes the treatment instrument distal end portion 121 into the biliary tract 111, the surgeon guides the insertion portion 100 into the biliary tract 111. On the occasion of the guidance, the surgeon causes the insertion portion 100 to advance in such a manner as to be along the treatment instrument insertion portion 122 of the catheter 120 with the balloon.

However, when the insertion portion 100 is inserted into the biliary tract 111, the following difference occurs in guidance of the insertion portion 100 between in the case that the rigidity of the treatment instrument insertion portion 122 disposed in the biliary tract 111 is flexible and in the case in which the rigidity is rigid.

The rigidity of the treatment instrument insertion portion 122 being flexible refers to a state in which the treatment instrument insertion portion 122 easily bends (also described as a first flexibility). More specifically, when the treatment instrument insertion portion 122 has the first flexibility, in a state in which the insertion portion 122 is inserted through an inside of the treatment instrument channel which passes through an inside of the bending portion 102, the bending portion 102 smoothly bends into a desired bending state with an operation of the bending lever.

In contrast with this, the rigidity of the treatment instrument insertion portion 122 being rigid refers to a state in which the treatment instrument insertion portion 122 is difficult to bend (also described as a second flexibility). More specifically, the flexibility is such a flexibility that makes it difficult to change the bending portion 102 into the desired bending state shown in, for example, the aforementioned FIG. 1 with the operation of the bending lever, in the state in which the insertion portion 122 is inserted through the inside of the treatment instrument channel which passes through the inside of the bending portion 102, when the treatment instrument insertion portion 122 has the first flexibility.

In the case in which the treatment instrument insertion portion 122 which is inserted into the biliary tract 111 has the first flexibility, when the surgeon operates the bending lever (not illustrated), the bending portion 102 is brought into a desired bending state with the bending lever operation, even if the treatment instrument insertion portion 122 is in such a state as to be disposed inside the bending portion 102.

Accordingly, the surgeon can easily cause the distal end portion 101 of the insertion portion 100 to face the outlet 112 of the biliary tract 111 in the state in which the treatment instrument insertion portion 122 is disposed in the bending portion 102. In addition, the surgeon can smoothly perform the catheter introducing manipulation and the catheter fixing manipulation thereafter.

However, when the surgeon shifts to the insertion portion introducing manipulation and starts pushing of the insertion portion 100, the insertion portion 100 is not guided into the biliary tract 111, and a curved shape of the treatment instrument insertion portion 122 changes from a large curved shape R shown by the broken line of FIG. 3 to a small curved shape r shown by the two-dot chain line. More specifically, the insertion portion 100 moves in the duodenum 110 as shown by the arrow Y3 in the drawing without advancing along the treatment instrument insertion portion 122, and the treatment instrument insertion portion 122 which is inserted through the inside of the treatment instrument channel is gradually changed into a strained state.

In contrast with this, when the treatment instrument insertion portion 122 inserted in the biliary tract 111 has the second flexibility, the shape of the treatment instrument insertion portion 122 is kept to be the curved shape R. As a result, when the surgeon shifts to the insertion portion introducing manipulation, the distal end portion 101 of the insertion portion 100 is inserted to a desired position in the biliary tract 111 along the treatment instrument insertion portion 122 as shown by the two-dot chain line of FIG. 4.

However, in the catheter introducing manipulation, when the surgeon operates the bending lever in the state in which the treatment instrument insertion portion 122 with the second flexibility is disposed in the bending portion 102, the bending portion 102 cannot be changed into a desired bending shape. As a result, the distal end portion 101 of the insertion portion 100 is disposed at a position different from the desired direction of the surgeon as shown in FIG. 5, and it becomes difficult to control a protruding direction of the treatment instrument insertion portion 122.

Therefore, when the treatment instrument insertion portion 122 has the second flexibility, the necessity to change the operation procedure as shown as follows, for example, arises.

The surgeon operates the bending lever in the state in which the treatment instrument insertion portion 122 is disposed at a rear side from the bending portion 102. As a result, the distal end portion 101 faces the outlet 112 of the biliary tract 111 as shown in the aforementioned FIG. 1. Thereafter, the surgeon causes the treatment instrument insertion portion 122 to pass through the inside of the bending portion 102 which is bent to insert the treatment instrument insertion portion 122 into the biliary tract 111.

However, the treatment instrument insertion portion 122 with the second flexibility has high straightness. Therefore, when the treatment instrument insertion portion 122 is inserted into the biliary tract 111 with the aforementioned procedure, there is the fear of occurrence of the problem that the insertion portion 122 cannot smoothly pass through the inside of the bending portion 102, the situation in which the treatment instrument insertion portion 122 which protrudes from the distal end portion 101 moves in a straight line inside the biliary tract 111 as shown by the arrow Y6 of FIG. 6, or the like. When the treatment instrument insertion portion 122 moves in a straight line in the biliary tract 111, there arises the fear of the treatment instrument distal end portion 121 contacting an inner wall.

As above, in the treatment instrument insertion portion of the catheter with the balloon, the disposition enabling flexibility which enables the treatment instrument distal end portion to be easily disposed at a desired position in the biliary tract, and the guidance enabling flexibility which enables the distal end portion of the insertion portion to be guided to a desired position in the biliary tract along the treatment instrument insertion portion are required.

Japanese Patent Application Laid-Open Publication No. 2007-319668 shows a medical catheter which has a distal end portion which can be inserted into a body cavity of a patient, has a first soft catheter segment, and has a second soft catheter segment which is disposed at a distal side of the first soft catheter segment. The medical catheter is configured so as to make only the first soft catheter segment hard and soft, and is configured so as to make only the second soft catheter segment hard and soft.

SUMMARY OF THE INVENTION

An insertion portion rigidity changeable catheter with a balloon according to one aspect of the present invention has an insertion portion including a coil-shaped member which is extensible and contractible, and includes a predetermined elastic force, with a compression length set to be a predetermined length, and a sheath which is a tube body with predetermined flexibility having a fluid conduit, includes a sheath main body surrounded by the coil-shaped member, and a sheath end portion provided at one end side of the sheath main body, having a diameter larger than the sheath main body and having a contact surface which one end surface of the coil-shaped member contacts, has one opening of the fluid conduit in the sheath end portion and has another opening of the fluid conduit at another end side of the sheath main body, an inflatable/deflatable balloon which is provided at the sheath end portion of the sheath, and is configured to be inflated by being supplied with a fluid via the one opening of the fluid conduit to extend an outside diameter dimension to be a diameter larger than an outside diameter of the sheath end portion, and to be deflated by the fluid being discharged via the one opening to be brought into close contact with an outer circumferential face of the sheath end portion, and an operation section which is fixedly provided at another end side of the sheath, and includes an operation section main body including a fluid supply and discharge apparatus connection portion which is directly or indirectly connected to a fluid supply and discharge apparatus which performs supply of the fluid into the balloon via the fluid conduit, or discharge of the fluid in the balloon, and a slide member which is slidably disposed in an inner surface side of the operation section main body, and is disposed at another end side of the operation section main body by an elastic force which the coil-shaped member has, wherein the fluid supply and discharge apparatus connection portion is fixed to the operation section main body, and the slide member is provided by having a configuration in which the slide member freely advances and retracts with respect to the fluid supply and discharge apparatus connection portion.

DETAILED DESCRIPTION OF THE PREFERRED EMBODIMENT

Hereinafter, an embodiment of the present invention will be described with reference to FIGS. 7 to 11.

Figure 1:
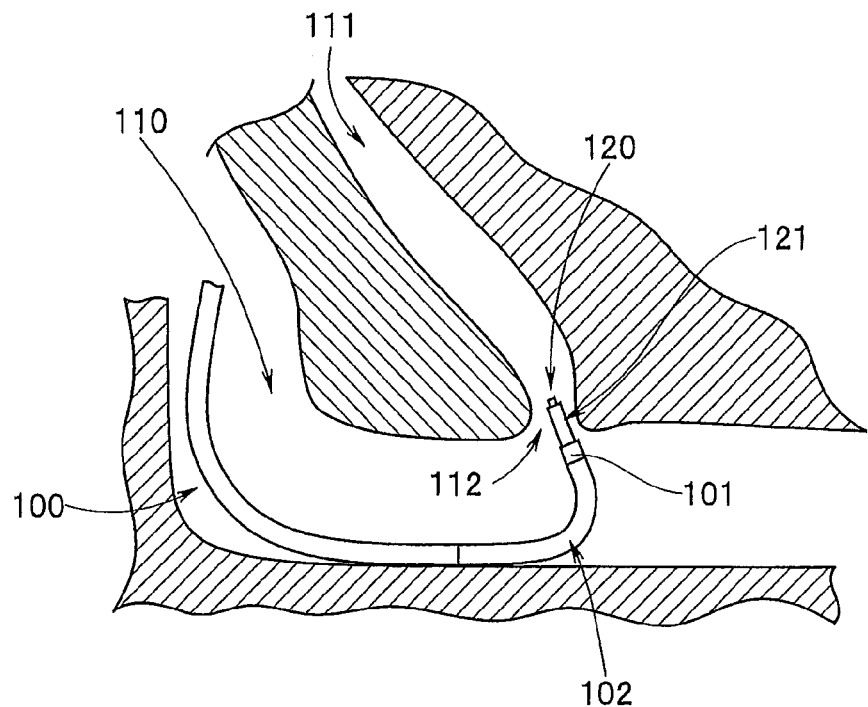
FIG. 1 is a view relating to a manipulation of inserting an insertion portion into a biliary tract, and explaining a catheter introducing manipulation.
Figure 2:
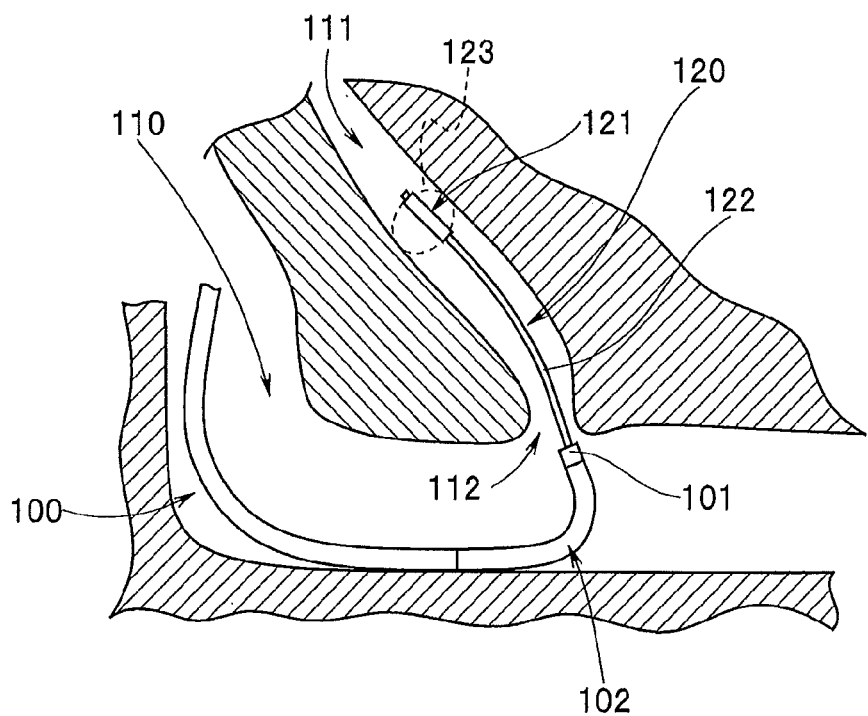
FIG. 2 is a view relating to the manipulation of inserting the insertion portion into the biliary tract, and explaining a catheter fixing manipulation.
Figure 3:
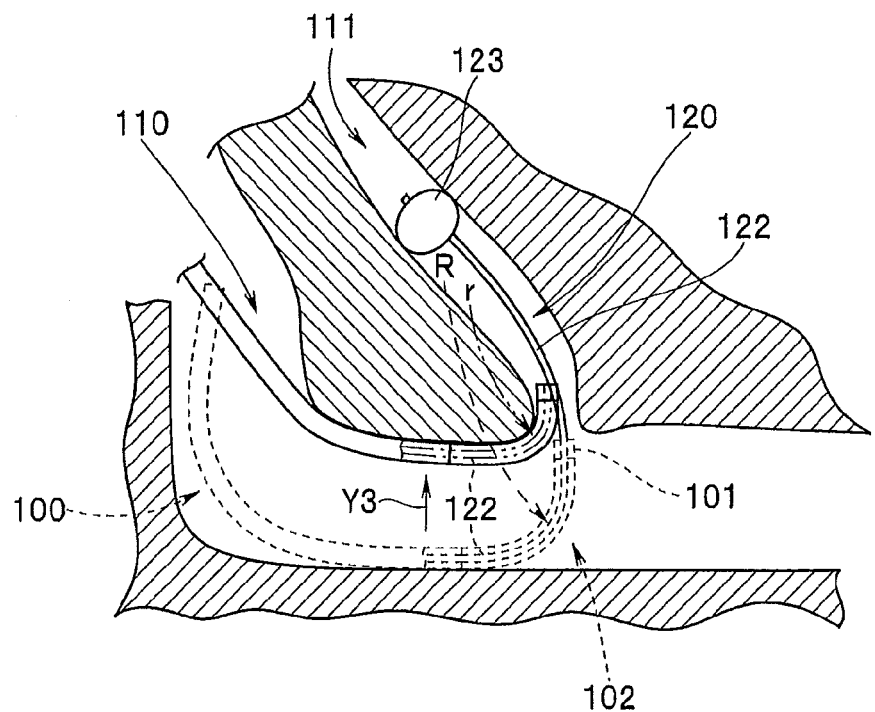
FIG. 3 is a view relating to the manipulation of inserting the insertion portion into the biliary tract, and explaining a relation of the insertion portion and a treatment instrument insertion portion in an insertion portion introducing manipulation in a case of the treatment instrument insertion portion having a first flexibility.
Figure 4:
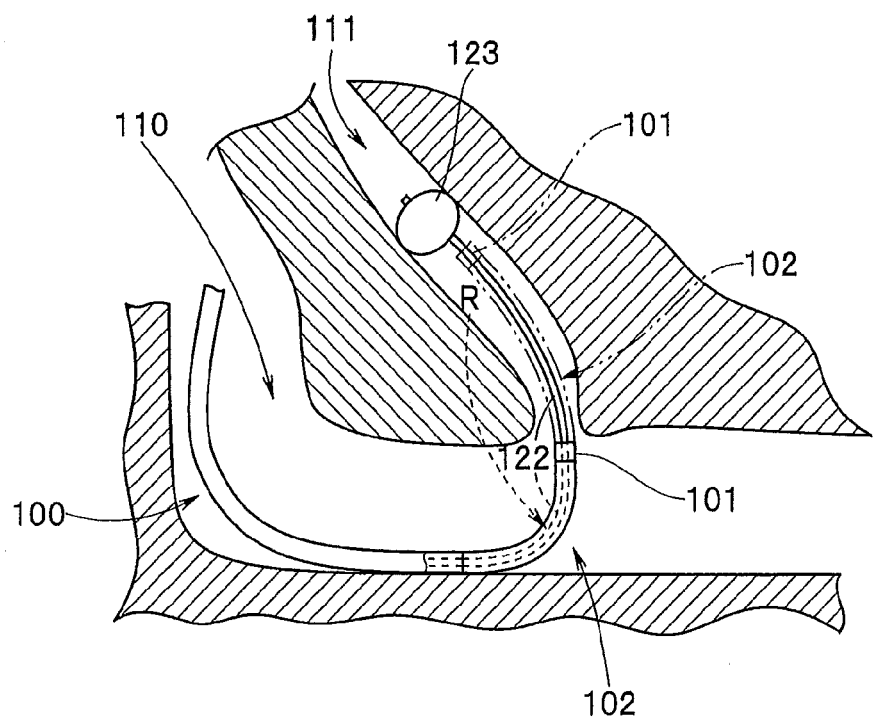
FIG. 4 is a view relating to the manipulation of inserting the insertion portion into the biliary tract, and explaining a relation of the insertion portion and the treatment instrument insertion portion in the insertion portion introducing manipulation in a case of the treatment instrument insertion portion having a second flexibility.
Figure 5:
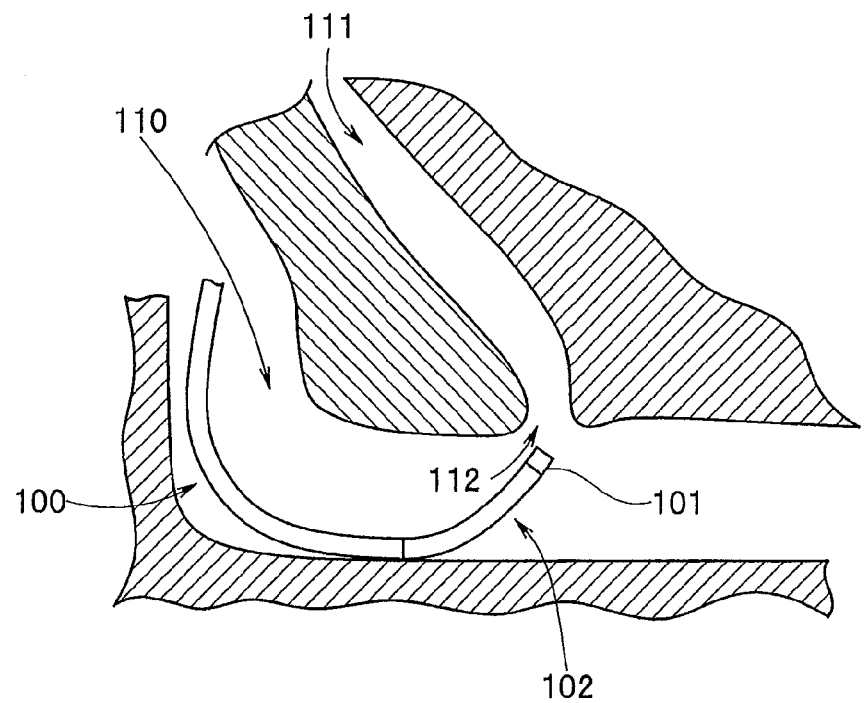
FIG. 5 is a view relating to the manipulation of inserting the insertion portion into the biliary tract, and explaining one example of a problem of the catheter introducing manipulation in the case of the treatment instrument insertion portion having the second flexibility.
Figure 6:
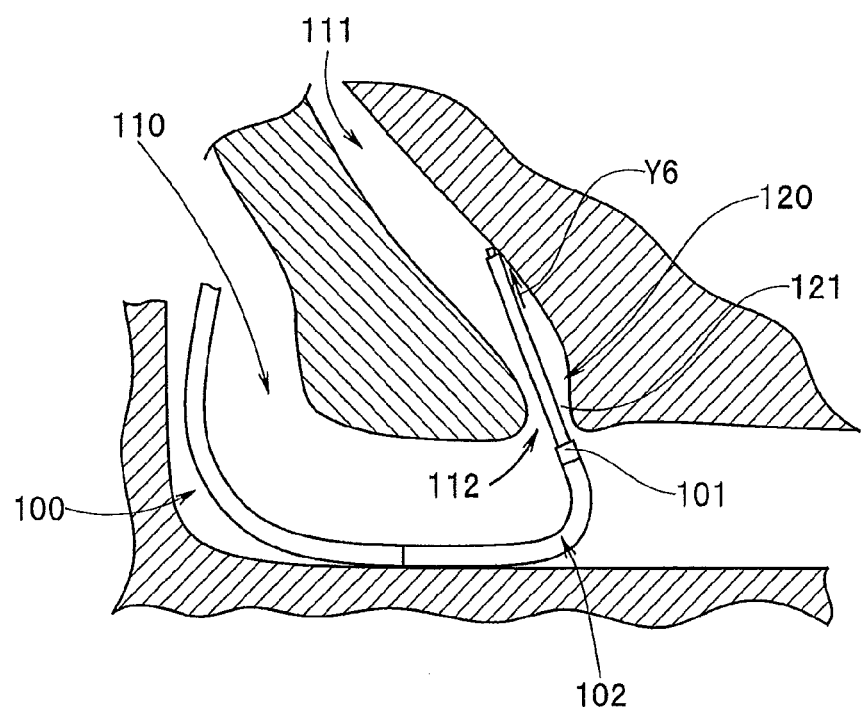
FIG. 6 is a view relating to the manipulation of inserting the insertion portion into the biliary tract, and explaining another example of the problem of the catheter introducing manipulation in the case of the treatment instrument insertion portion having the second flexibility.
Figure 7:
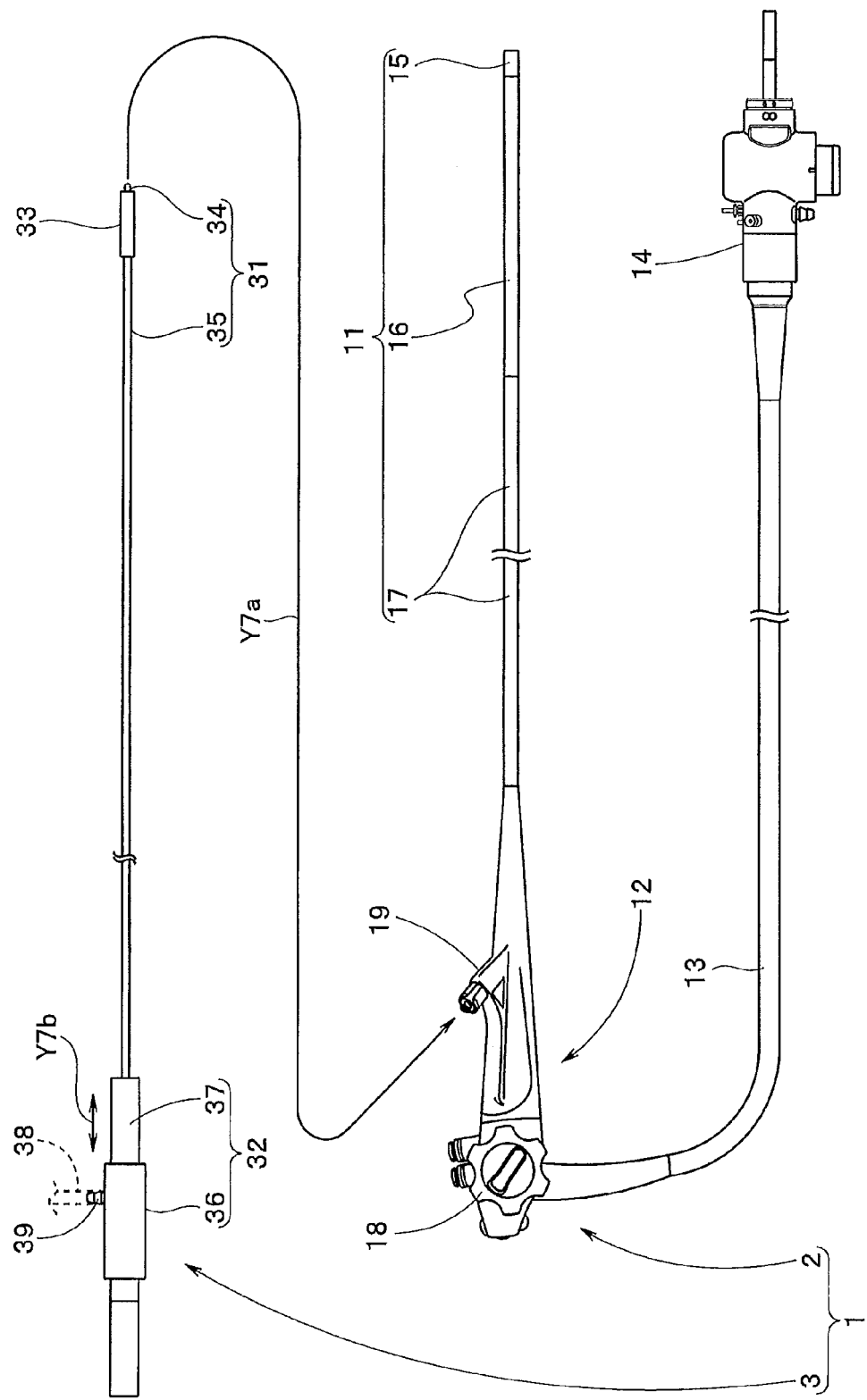
FIG. 7 is a view explaining an endoscope system including an endoscope, and an insertion portion rigidity changeable catheter with a balloon.

As shown in FIG. 7, an endoscope system 1 is configured by including an endoscope 2, and an insertion portion rigidity changeable catheter with a balloon (hereinafter, abbreviated as a catheter) 3.

The endoscope 2 is configured by including an elongated endoscope insertion portion 11 having flexibility, an endoscope operation section 12 provided at a proximal end side of the endoscope insertion portion 11, and a universal cord 13 which is extended from a side portion of the endoscope operation section 12 and has flexibility. An endoscope connector 14 which is detachably connected to, for example, a light source apparatus (not illustrated) which is an outside apparatus is provided at an end portion of the universal cord 13.

The endoscope insertion portion 11 is configured by a distal end portion 15, a bending portion 16 and a flexible tube portion 17 having flexibility being connectively provided in sequence from a distal end side. The bending portion 16 is configured to bend in, for example, a vertical direction. The endoscope operation section 12 is provided with a bending operation device 18 for performing bending operation of the bending portion 16. Reference sign 19 designates a treatment instrument insertion port. A treatment instrument such as the catheter 3 is inserted into a treatment instrument channel (not illustrated) via the treatment instrument insertion port 19 as shown by the arrow Y7a, and is led out into a body from a channel distal end opening (not illustrated).

The catheter 3 is configured by mainly including a catheter insertion portion 31, a catheter operation section 32 and a balloon 33. The catheter insertion portion 31 has a configuration in which flexibility changes. The catheter operation section 32 changes the flexibility of the catheter insertion portion 31. The balloon 33 is inflatable, and is disposed at a distal end portion of the catheter insertion portion 31.

The catheter insertion portion 31 is configured by including a sheath 34 and a coil-shaped member 35. The catheter operation section 32 is configured by including an operation section main body 36 and a slide member 37. The slide member 37 freely advances and retracts as shown by the arrow Y7b with respect to the operation section main body 36. Here, a state of the catheter operation section 32 shown in the drawing is the state in which the flexibility of the catheter insertion portion 31 is changed to a second flexibility which is the most rigid. In this case, the slide member 37 is advanced with respect to the operation section main body 36.

Reference sign 38 designates a fluid tube. The fluid tube 38 is extended from a fluid supply and discharge apparatus (not illustrated) which is an outside apparatus. Reference sign 39 designates a fluid supply and discharge apparatus connection portion (hereinafter, abbreviated as a fluid pipe sleeve), and the fluid tube 38 is connected to the fluid supply and discharge apparatus connection portion.

The fluid supply and discharge apparatus connection portion is not limited to the fluid pipe sleeve 39, and may be a lure pipe sleeve to which a syringe that is the fluid supply and discharge apparatus is connected.

Figure 8:
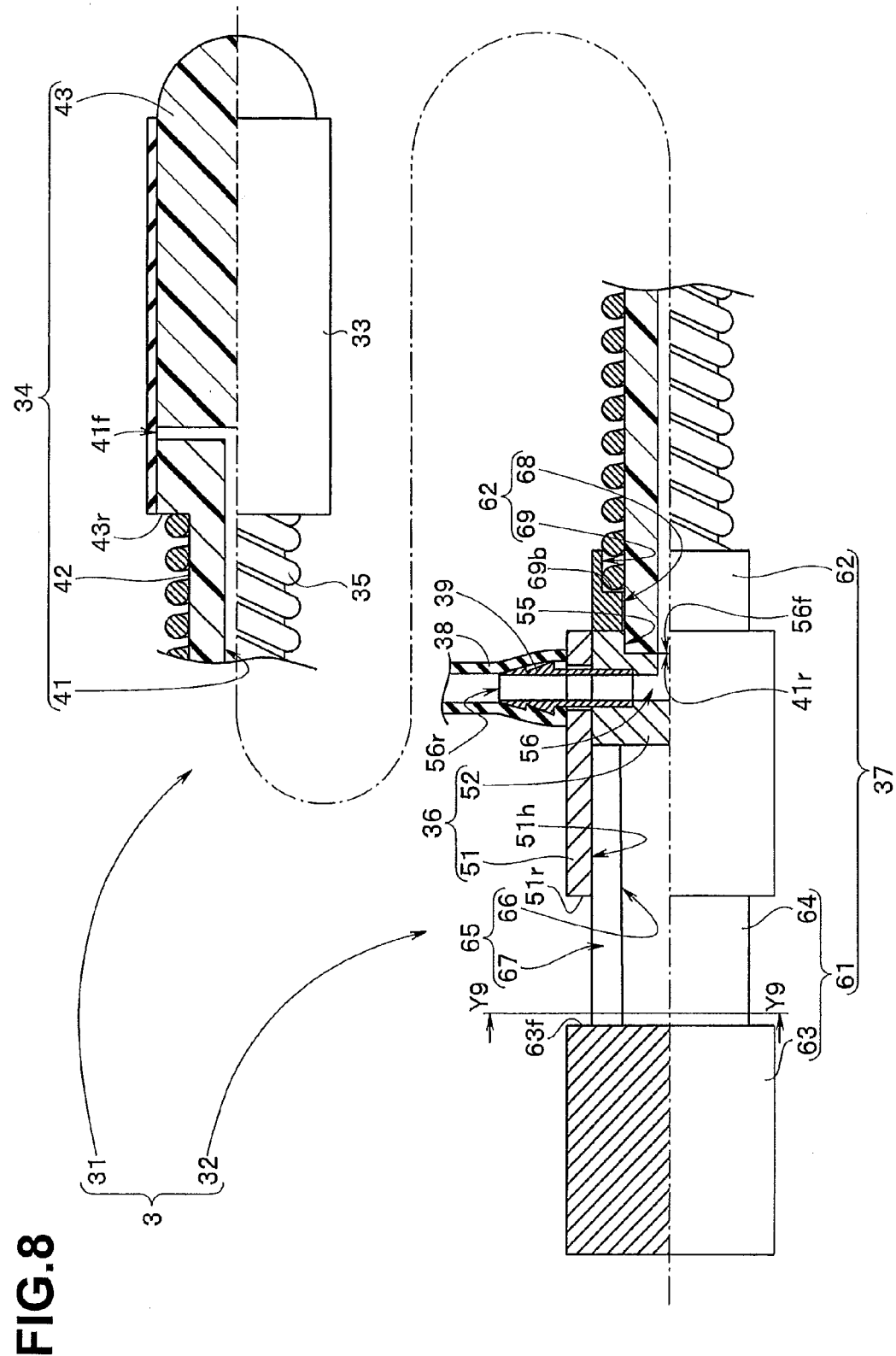
FIG. 8 is a view explaining an insertion portion rigidity changeable catheter with a balloon in which an operation state of an operation section is a first operation state, and a coil-shaped member has a natural length.

With reference to FIG. 8, a configuration of the catheter 3 will be described in detail.

The sheath 34 is a tube body which has a fluid path 41 for a sheath and has a predetermined flexibility. The sheath 34 is configured by including a sheath main body 42 and a sheath end portion 43. The sheath main body 42 is surrounded by the coil-shaped member 35. The sheath end portion 43 is provided at one end side of the sheath main body 42. The balloon 33 is mounted to the sheath end portion 43.

The sheath end portion 43 is larger in diameter than the sheath main body 42. The sheath end portion 43 includes a contact surface 43*r* which one end surface of the coil-shaped member 35 contacts. An opening 41*f* for a balloon is formed within a balloon mounting range of the sheath end portion 43. The opening 41*f* for the balloon is one opening of the fluid path 41 for the sheath. The other opening of the fluid path 41 for the sheath is formed in another end surface of the sheath main body 42 as a tube proximal end opening 41*r*.

Meanwhile, the coil-shaped member 35 is an elongated coil spring. The coil-shaped member 35 has predetermined wire diameter and pitch, and a predetermined elastic force, and is configured to be deformed to have a predetermined compression length with a predetermined natural length.

In the present embodiment, a length of the sheath main body 42 is set to be longer than the natural length of the coil-shaped member 35 by a predetermined length.

The balloon 33 is in, for example, a pipe shape. A distal end side and a proximal end side of the balloon 33 are fixed to an outer circumferential face of the sheath end portion 43 of the sheath 34 by adhesion, or bobbin adhesion. The balloon 33 is inflated into a substantially sphere shape by being supplied with a fluid such as air or water into the balloon 33 via the opening 41*f* for the balloon. The balloon 33 is configured so that an outside diameter dimension is increased to be a larger diameter than an outside diameter of the sheath end portion 43 (see FIGS. 10 and 11), and is disposed in close contact with, for example, a wall of a biliary tract.

The balloon 33 is contracted by discharging the fluid supplied into the balloon 33 from the opening 41*f* for the balloon, and is brought into close contact with the outer circumferential face of the sheath end portion 43 as shown in the present drawings.

Figure 9:
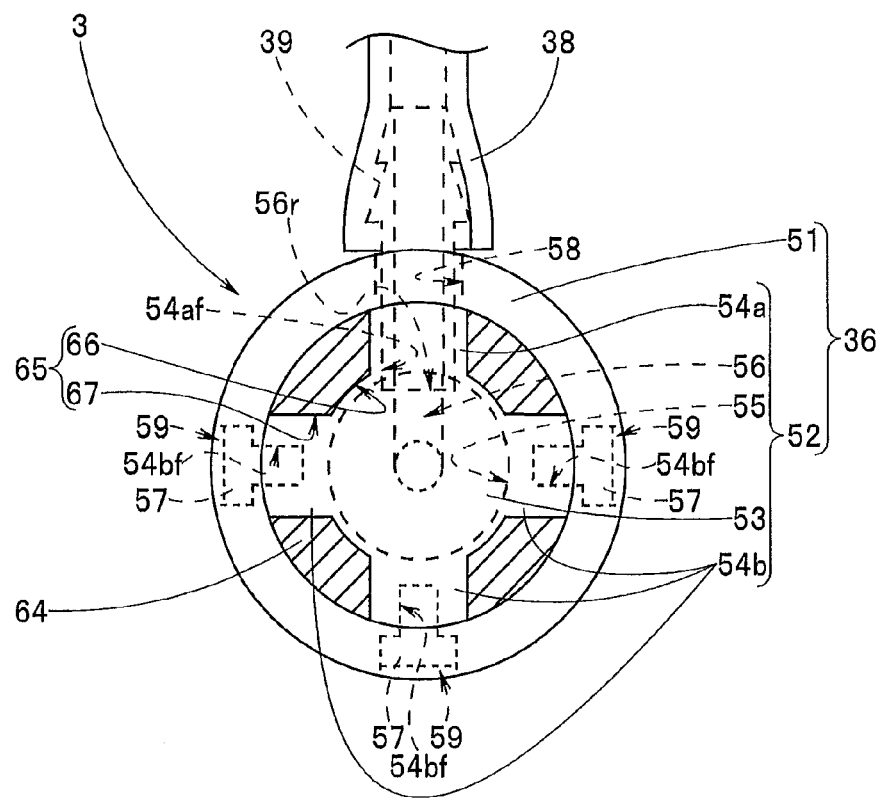
FIG. 9 is a sectional view taken along the line of the arrows Y9-Y9 of FIG. 8.

As shown in FIGS. 8 and 9, the operation section main body 36 is configured by including an operation section exterior body 51 which also functions as a grasping portion, and a sheath fixing member 52.

The operation section exterior body 51 is in a pipe shape including an axial direction through-hole 51*h*. The sheath fixing member 52 is integrally fixed at a predetermined position in the axial direction through-hole 51*h*. Further, in the axial direction through-hole 51*h*, a first cylinder portion 61 which configures the slide member 37 and will be described later is slidably disposed.

The sheath fixing member 52 is fixedly provided at another end portion of the sheath main body 42 which protrudes from the coil-shaped member 35. The sheath fixing member 52 includes a cylindrical portion 53, a plurality of, for example, four of projected portions 54, a recessed portion 55 for the sheath, and an operation section fluid path 56. The operation section fluid path 56 is in a folded shape. The operation section fluid path 56 has an operation section distal end opening 56*f* and a pipe sleeve communication port 56*r*.

The cylindrical portion 53 is disposed in an inner hole, which will be described later, of the first cylinder portion 61. The projected portions 54 are protruded from an outer circumferential face of the cylindrical portion 53, and are formed equidistantly (intervals of 90 degrees in FIG. 9) in a circumferential direction. An outer circumferential face of the projected portion 54 is disposed in contact with an inner surface of the operation section exterior body 51.

In the present embodiment, the operation section exterior body 51 and the sheath fixing member 52 are integrally fixed by fixing screws 57. Therefore, of the plurality of projected portions 54, one is a projected portion 54*a* for a fluid, and the remaining projected portions 54 are fixing projected portions 54*b*. A second female screw portion 54*bf* in which the fixing screw 57 is screwed is formed on an outer circumferential face side of the fixing projected portion 54*b*. In an outer circumferential face side of the projected portion 54*a* for a fluid, a first female screw portion 54*af* which fixes the fluid pipe sleeve 39 by, for example, screwing, and a pipe sleeve communication port 56*r* are formed.

In the configuration, at a predetermined position in an outer circumferential face of the operation section exterior body 51, a relief hole 58 for a pipe sleeve and a screw hole 59 are formed. The relief hole 58 for the pipe sleeve corresponds to the fluid pipe sleeve 39. The screw hole 59 corresponds to the second female screw portion 54bf. The screw hole 59 has a recessed portion in which a head portion of the fixing screw 57 is disposed and a relief hole through which the screw portion passes.

The recessed portion 55 for the sheath is a hole which is formed at one end surface side of the sheath fixing member 52. The other end portion of the sheath main body 42 is disposed in the recessed portion 55 for the sheath. The operation section distal end opening 56f is included in a bottom surface of the recessed portion 55 for the sheath. The other end portion of the sheath main body 42 is disposed in the recessed portion 55 for the sheath, and is integrally fixed to the sheath fixing member 52 by, for example, adhesion. As a result, the operation section distal end opening 56f of the operation section fluid path 56 and the tube proximal end opening 41r of the fluid path 41 for the sheath are in a communicating state.

According to the configuration, for example, air which is supplied to the fluid tube 38 from the fluid supply and discharge apparatus which is an outside apparatus is supplied into the balloon 33 via the fluid pipe sleeve 39, the pipe sleeve communication port 56r, the operation section fluid path 56, the operation section distal end opening 56f, the tube proximal end opening 41r, the fluid path 41 for the sheath, and the opening 41f for the balloon.

The slide member 37 is configured by including, for example, a first cylinder portion 61 which also functions as a grasping portion, and a second cylinder portion 62 having a coil contact portion.

The first cylinder portion 61 includes a large diameter portion 63 which is the grasping portion, and a slide portion 64 which slides with respect to the sheath fixing member 52. In the present embodiment, an outside diameter dimension of the large diameter portion 63 and an outside diameter dimension of the operation section exterior body 51 are set to be substantially the same diameter.

An outside diameter dimension of the slide portion 64 is smaller than the outside diameter dimension of the large diameter portion 63. The slide portion 64 is set to be engaged in the axial direction through-hole 51h of the operation section exterior body 51 by a predetermined fit. Accordingly, the slide portion 64 is capable of smoothly advancing and retracting in the axial direction through-hole 51h of the operation section exterior body 51.

The slide portion 64 has a slide hole 65. The slide hole 65 is configured by including an inner hole 66 in which the cylindrical portion 53 is disposed, and four notches 67 which respectively correspond to the four projected portions 54. An axis of the inner hole 66 corresponds to a longitudinal axis of the slide member 37. A front end face of the slide portion 64 has an opening. A position of a bottom surface of the inner hole 66 is the same position as one end surface of the large diameter portion 63, or a position deeper than the one end surface by a predetermined dimension as shown by the broken line.

In contrast with this, the notch 67 is a radial groove which allows the inner hole 66 and an outer circumferential face outer side to communicate with each other. The dimension of the length of the notch 67 is set to be the same as an amount of movement which brings the coil-shaped member 35 into a close contact state, or to be longer than the amount of movement by a predetermined amount.

The second cylinder portion 62 includes an axial direction through-hole 68 and a recessed portion 69. The sheath main body 42 can pass in the axial direction through-hole 68. In the recessed portion 69, the other end portion of the coil-shaped member 35 surrounding the sheath main body 42 is placed. A center axis of the axial direction through-hole 68 and a center axis of the recessed portion 69 are coaxial with a longitudinal axis of the second cylinder portion 62. Reference sign 69b designates a bottom surface. The bottom surface 69b is a contact surface with another end surface of the coil-shaped member 35.

The second cylinder portion 62 is integrally fixed to the first cylinder portion 61 by adhesion, screwing, a screw or the like which is a fastening member.

The slide member 37 in which the first cylinder portion 61 and the second cylinder portion 62 are integrally fixed is slidable with respect to the operation section main body 36 in which the operation section exterior body 51 and the sheath fixing member 52 are integrated.

In a first operation state of the catheter operation section 32, a rigidity of the catheter insertion portion 31 is a first flexibility which is flexible. When the catheter operation section 32 is in the first operation state, another end surface of the second cylinder portion 62 of the slide member 37 is in contact with one end surface of the sheath fixing member 52 of the operation section main body 36. In the first operation state, the coil-shaped member 35 surrounding the sheath main body 42 has a natural length. Accordingly, the rigidity of the catheter insertion portion 31 is flexible.

In contrast with this, in a second operation state of the catheter operation section 32, the rigidity of the catheter insertion portion 31 has a second flexibility which is rigid. When the catheter operation section 32 is in the second operation state, one end surface 63f of the first cylinder portion 61 which configures the first cylinder portion 61 of the slide member 37 contacts the other end surface 51r of the operation section exterior body 51 of the operation section main body 36. In the second operation state, the coil-shaped member 35 surrounding the sheath main body 42 is compressed to be in a close contact state. Accordingly, the rigidity of the catheter insertion portion 31 is rigid.

More specifically, the catheter insertion portion 31 is configured to obtain the first flexibility and the second flexibility by the operation state being changed to the first operation state and the second operation state by the slide member 37 of the catheter operation section 32 being advanced and retracted.

The first flexibility and the second flexibility in the present embodiment are similar to the case in which a rigidity of a treatment instrument insertion portion 122 described above is flexible or rigid.

More specifically, when the catheter insertion portion 31 has the first flexibility, even in the state in which the catheter insertion portion 31 is inserted through the inside of the treatment instrument channel in the bending portion 16 of the endoscope insertion portion 11, the bending portion 16 smoothly bends in the desired bending state with operation of the bending operation device 18.

Meanwhile, when the catheter insertion portion 31 has the second flexibility, the endoscope insertion portion 11 can be caused to advance and retract along the catheter insertion portion 31 in the curved shape.

Further, in the present embodiment, in order that the coil-shaped member 35 has a natural length in the first operation state of the catheter operation section 32, the length of the coil-shaped member 35 and a distance from the bottom surface 69b to the contact surface 43r are set so that a gap is formed in any one of between the one end of the coil-shaped member 35 and the contact surface 43r, and between the other end of the coil-shaped member 35 and the bottom surface 69b.

An operation of the endoscope system 1 including the catheter 3 which is configured as described above and the endoscope 2 will be described.

Figure 10:
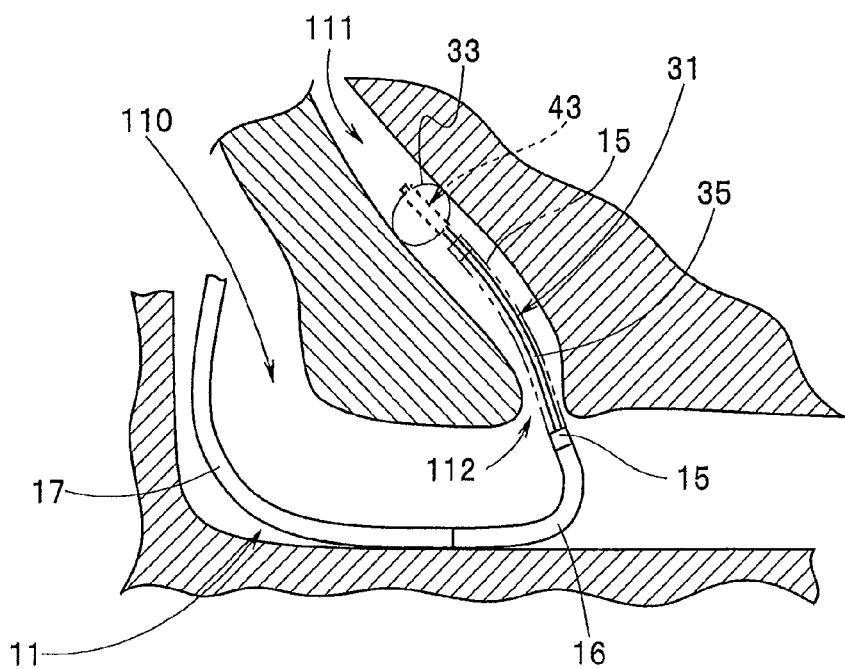
FIG. 10 is a view explaining an operation of the endoscope system including the insertion portion rigidity changeable catheter with a balloon and an endoscope, and explaining a procedure of inserting the insertion portion of the endoscope located in a duodenum through an inside of the biliary tract with use of the insertion portion rigidity changeable catheter with a balloon.

As shown in FIG. 10, a manipulation of inserting the endoscope insertion portion 11 into a biliary tract 111 from a duodenum 110 will be described.

First, in performing the above described manipulation, a surgeon inserts the distal end portion 15 of the endoscope insertion portion 11 to a vicinity of a biliary tract outlet 112 which is a duodenum opening of the biliary tract 111. At this time, the catheter insertion portion 31 with the first flexibility is inserted through the inside of the treatment instrument channel included by the endoscope insertion portion 11.

Next, the surgeon properly performs bending operation of the bending operation device 18 provided at the endoscope operation section 12, and causes the front end face of the distal end portion 15 to face the biliary tract outlet 112. Thereafter, the surgeon performs a catheter introducing manipulation, a catheter fixing manipulation and an insertion portion introducing manipulation, and disposes the endoscope insertion portion 11 in the biliary tract 111.

In the catheter introducing manipulation, the surgeon leads the distal end portion of the catheter insertion portion 31 with the first flexibility from the opening of the treatment instrument channel. Subsequently, the surgeon disposes the distal end portion of the catheter insertion portion 31 in the vicinity of the outlet 112 of the biliary tract 111. Thereafter, the surgeon inserts the catheter insertion portion 31 into the biliary tract 111 by a predetermined amount from the distal end face of the endoscope insertion portion 11. Thereby, the balloon 33 which is provided at the catheter insertion portion 31 is disposed at a desired position in the biliary tract 111.

In the catheter fixing manipulation, the surgeon supplies air to the balloon 33 via the fluid tube 38 from the fluid supply and discharge apparatus which is the outside apparatus. Thereupon, the balloon 33 is inflated and is brought into close contact with the inner wall of the biliary tract 111 by a predetermined closely contacting force as shown by the solid line of FIG. 10. As a result, the catheter insertion portion 31 is fixed to the desired position in the biliary tract 111.

Figure 11A:
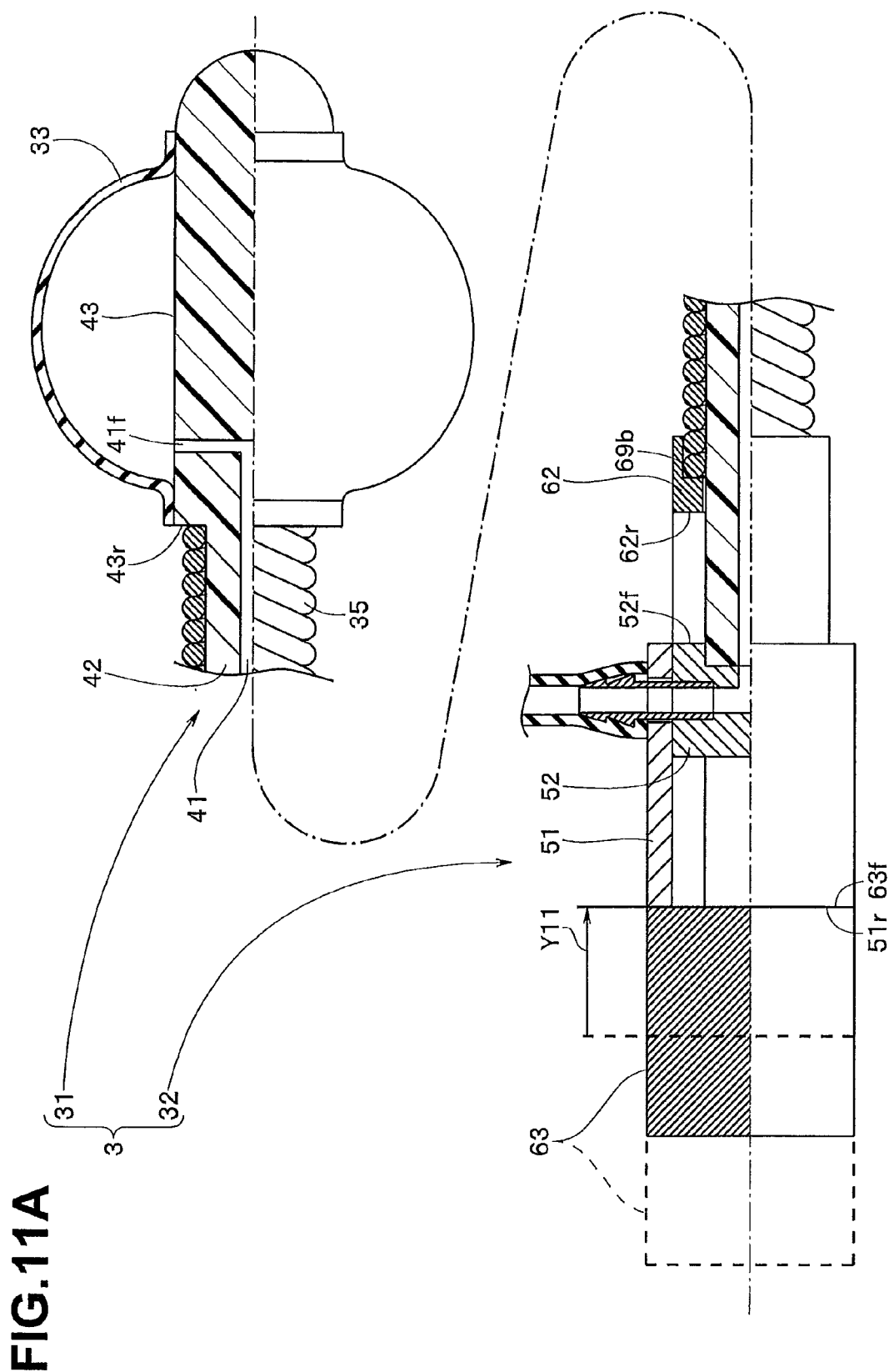
FIG. 11A is a view explaining the insertion portion rigidity changeable catheter with a balloon in which the operation state of the operation section is in a second operation state and the coil-shaped member is in close contact therewith.

Here, the surgeon performs an operation of changing the operation state of the catheter operation section 32 to the second operation state from the first operation state in order to change the catheter insertion portion 31 with the first flexibility to the second flexibility. More specifically, the surgeon performs a hand operation of moving the first cylinder portion 61 which the surgeon grasps with, for example, the right hand to the operation section exterior body 51 which the surgeon grasps with the left hand as shown by the arrow Y11 in the longitudinal axis direction against the elastic force of the coil-shaped member 35, as shown in FIG. 11. Subsequently, the surgeon causes the one end surface 63f of the first cylinder portion 61 to contact the other end surface 51r of the operation section exterior body 51.

Thereupon, the second cylinder portion 62 is caused to advance in the balloon 33 direction, and the bottom surface 69b of the advancing second cylinder portion 62 contacts the other end of the coil-shaped member 35. Thereafter, as the second cylinder portion 62 advances, the distance between the contact surface 43r and the bottom surface 69b becomes shorter. Thereupon, the coil-shaped member 35 with a natural length is compressed and is brought into a close contact state as described above. As a result, the rigidity of the catheter insertion portion 31 is switched to the second flexibility.

In the insertion portion introducing manipulation, the surgeon causes the endoscope insertion portion 11 to advance along the catheter insertion portion 31 and guides the endoscope insertion portion 11 into the biliary tract 111. At this time, the catheter insertion portion 31 has the second flexibility, and therefore, the curved shape of the catheter insertion portion 31 is kept to be a large curved shape R. As a result, the distal end portion 15 of the endoscope insertion portion 11 is inserted to a desired position in the biliary tract 111 along the catheter insertion portion 31 as shown by the two-dot chain line in the drawing.

Thereafter, the surgeon successively performs the catheter introducing manipulation of the catheter insertion portion 31 to a biliary tract deep portion, extraction of the catheter insertion portion 31 from the treatment instrument channel, or the like. On the occasion, the surgeon performs an operation of returning the operation state of the catheter operation section 32 to the first operation state from the second operation state, and returns the catheter insertion portion 31 to the first flexibility. At this time, the surgeon performs a hand operation of moving the first cylinder portion 61 which the surgeon grasps with the right hand, in the opposite direction from the arrow Y11 with the elastic force of the coil-shaped member 35 as auxiliary power. Subsequently, the catheter insertion portion 31 returns to the first flexibility when the other end surface 62r of the second cylinder portion 62 contacts the one end surface 52f of the sheath fixing member 52.

As above, according to the catheter 3 of the present embodiment, the slide member 37 is configured to freely advance and retract with respect to the operation section main body 36. The configuration is such that at the time of the first operation state in which the second cylinder portion 62 is in contact with the sheath fixing member 52, the rigidity of the catheter insertion portion 31 becomes the first flexibility which is flexible, and at the time of the second operation state in which the first cylinder portion 61 and the operation section exterior body 51 are in contact with each other, the rigidity of the catheter insertion portion 31 becomes the second flexibility, which is rigid.

As a result, with one action operation which causes the slide member 37 to advance or retract in the longitudinal axis direction of the catheter operation section 32, the flexibility of the catheter insertion portion 31 can be easily switched to the second flexibility from the first flexibility, or to the first flexibility from the second flexibility.

In the embodiment described above, the gap is formed in any one of the spaces between the one end of the coil-shaped member 35 and the contact surface 43r and between the other end of the coil-shaped member 35 and the bottom surface 69b, and the coil-shaped member 35 has a natural length, whereby the catheter insertion portion 31 has the first flexibility.

However, the configuration may be adopted, which obtains the first flexibility of the catheter insertion portion 31 in the state in which the one end of the coil-shaped member 35 and the contact surface 43r are in contact with each other, and the other end of the coil-shaped member 35 and the bottom surface 69b are in contact with each other.

Further, the configuration may be adopted, in which at the time of the second operation state, a hook can be hooked on the projected portion. In this case, for example, a locking claw having a clasp portion, a so-called hook (not illustrated) is provided as a locking member at one of the operation section exterior body 51 and the first cylinder portion 61, and a locking portion, a so-called rod-shaped projected portion (not illustrated) is provided as a locked member on which the clasp portion of the locking claw can be hooked is provided at one of the operation section exterior body 51 and the first cylinder portion 61.

According to the configuration, the hook which is the locking claw is hooked on the projected portion which is the locked portion, whereby the catheter operation section 32 can be kept in the second operation state.

Furthermore, in the embodiment described above, after the balloon 33 inflated by being supplied with air is brought into close contact with and fixed to the inner wall of the biliary tract 111, the catheter insertion portion 31 with the first flexibility is changed to have the second flexibility. However, a catheter insertion portion 31A is configured as follows, whereby a rigidity of the catheter insertion portion 31A can be changed to be more rigid than the first flexibility at the same time as when the balloon 33 is inflated, without operation of the catheter operation section 32.

Figure 11B:
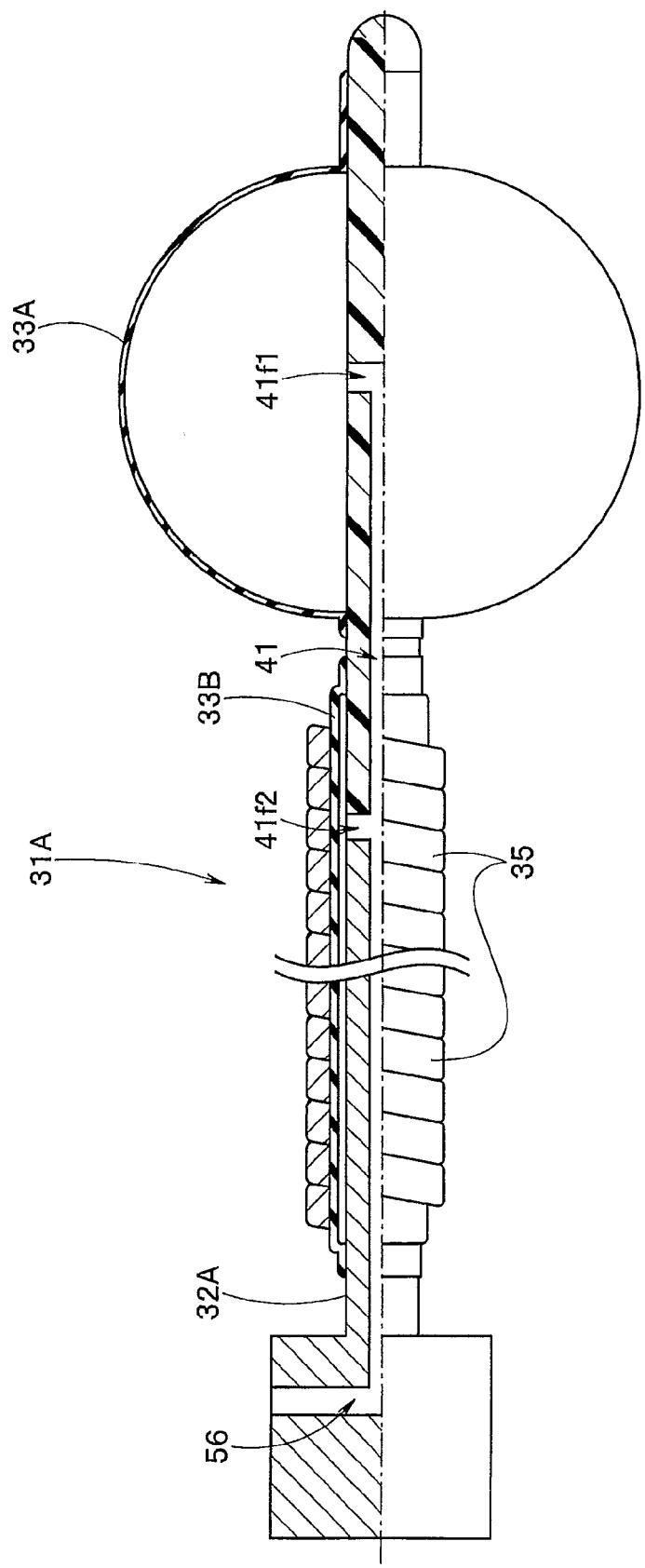
FIG. 11B is a view explaining the insertion portion rigidity changeable catheter with a balloon in which rigidity of a catheter insertion portion becomes rigid at the same time as when the balloon is inflated.

As shown in FIG. 11B, the catheter insertion portion 31A includes a first balloon 33A and a second balloon 33B. The first balloon 33A is provided at a distal end side of a sheath main body 42A and performs an action similar to the aforementioned balloon 33. The second balloon 33B is disposed in a gap between the sheath main body 42A and the coil-shaped member 35.

The sheath main body 42A includes the fluid path 41 for the sheath. The fluid path 41 for the sheath includes an opening 4112 for the second balloon in addition to an opening 41/1 for the first balloon. The opening 41/1 for the first balloon is provided within a first balloon mounting range at the distal end side of the sheath main body 42. The opening 4112 for the second balloon is provided in a second balloon mounting range in a central portion of the sheath main body 42.

The balloons 33A and 33B are in, for example, pipe shapes. Distal end sides and proximal end sides of the balloons 33A and 33B are fixed to the outer circumferential face of the sheath main body 42 by adhesion or bobbin adhesion.

According to the configuration, for example, air which is supplied to the fluid tube 38 from the fluid supply and discharge apparatus which is an outside apparatus is supplied into the fluid pipe sleeve 39, the pipe sleeve communication port 56r, the operation section fluid path 56, the operation section distal end opening 56f, the tube proximal end opening 41r and the fluid path 41 for the sheath, thereafter, is supplied into the first balloon 33A via the opening 41/1 for the first balloon, and is supplied into the second balloon 33B via the opening 4112 for the second balloon.

An operation of the catheter insertion portion 31A having the balloons 33A and 33B will be described.

In the catheter introducing manipulation, a surgeon leads the distal end portion of the catheter insertion portion 31 with the first flexibility from the opening of the treatment instrument channel. Subsequently, the surgeon disposes the distal end portion of the catheter insertion portion 31 in the vicinity of the outlet 112 of the biliary tract 111. Thereafter, the surgeon inserts the catheter insertion portion 31 into the biliary tract 111 by a predetermined amount from the front end face of the endoscope insertion portion 11. Thereby, the first balloon 33A provided at the catheter insertion portion 31 is disposed at the desired position in the biliary tract 111.

In the catheter fixing manipulation, the surgeon supplies air from the fluid supply and discharge apparatus, which is the outside apparatus, via the fluid tube 38. Thereupon, the first balloon 33A is inflated and is brought into close contact with the inner wall of the biliary tract 111 with a predetermined closely contacting force. As a result, the catheter insertion portion 31A is fixed to a desired position in the biliary tract 111. In addition, the second balloon 33B is inflated in the gap between the sheath main body 42A and the coil-shaped member 35. Thereupon, the outer circumferential face of the second balloon 33B is brought into close contact with an inner surface of the coil-shaped member 35. As a result, the coil-shaped member 35 is difficult to move with respect to the sheath main body 42A, and the catheter insertion portion 33A is difficult to curve. In other words, the rigidity of the catheter insertion portion 31A becomes more rigid than the first flexibility.

As above, the first balloon 33A and the second balloon 33B are provided at the catheter insertion portion 31A, and the opening 41/1 for the first balloon and the opening 4112 for the second balloon are provided in the fluid path 41 for the sheath. As a result, the second balloon 33B is inflated at the same time as when the first balloon 33A is inflated, and the catheter insertion portion 31A is made rigid and can easily obtain the second flexibility.

A tube body (not illustrated) which prevents the coil-shaped member 35 from increasing in diameter is provided at an outer circumferential side of the coil-shaped member 35, and reduction in close contactability of the outer circumferential face of the second balloon 33B and the inner surface of the coil-shaped member 35 can be prevented.

Further, when the endoscope insertion portion 11 described above is inserted into the biliary tract 111 from the duodenum 110 side, the bending direction of the bending portion 16 is limited to the upper direction in FIG. 10, for example. Therefore, the distal end side of the coil-shaped member 35 of the catheter insertion portion 31 may be formed as shown in FIG. 12A, FIG. 12B or FIG. 13, and the bending performance to the biliary tract 111 from the duodenum 110 may be improved.

Figure 12A:
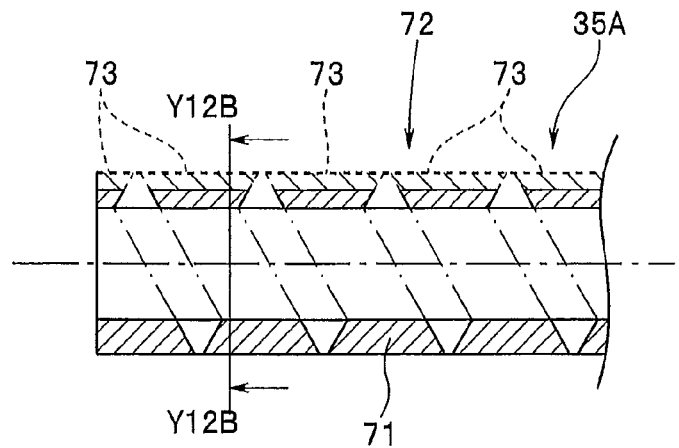
FIG. 12A is a view relating to another configuration example of the coil-shaped member which configures the catheter insertion portion, and explaining the coil-shaped member which is configured by an element wire with a sectional shape being a trapezoidal shape being wound around, and includes a cutoff portion at a predetermined portion at a distal end side portion.
Figure 13:
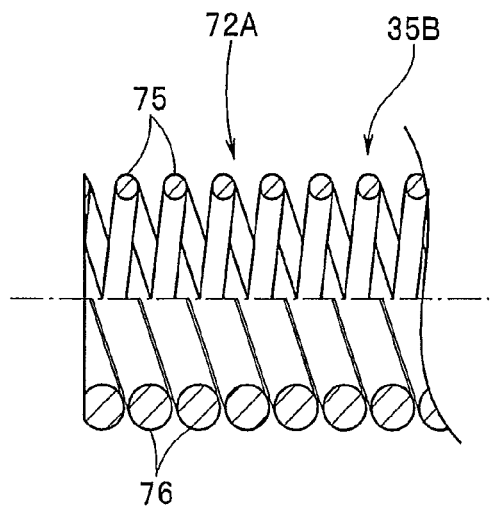
FIG. 13 is a view relating to another configuration example of the coil-shaped member configuring the catheter insertion portion, and explaining a coil-shaped member including a small-diameter wire winding portion formed by a small-diameter element wire, and a large-diameter wire winding portion formed by a large-diameter element wire at a predetermined portion at a distal end side portion by the element wire with an element wire diameter periodically changing being wound around.

More specifically, a coil-shaped member 35A of the catheter insertion portion 31 shown in FIG. 12A is such that an upper side which is a short side of an element wire 71 with a cross-sectional shape in a trapezoidal shape is wound around at predetermined pitches toward a center axis direction. The coil-shaped member 35A has a predetermined elastic force, has a predetermined natural length and is deformed to a predetermined compression length.

Figure 12B:
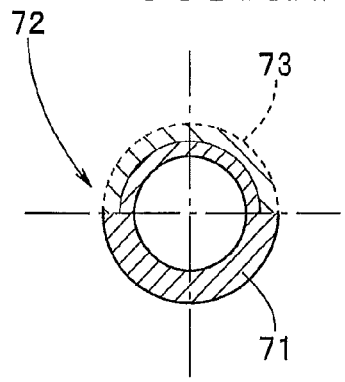
FIG. 12B is a sectional view taken along the line of the arrows Y12B to Y12B of FIG. 12A.

As shown in FIG. 12A and FIG. 12B, a bending characteristic changing portion is provided at a distal end side winding portion 72 of the coil-shaped member 35A. The bending characteristic changing portion is the portion in which a cutoff portion 73 shown by the oblique lines is formed in a half, for example, an upper half in the drawing, of an entire circumference of the distal end side winding portion 72, and the remaining portion is an unprocessed portion.

As a result, when the case in which the distal end side winding portion 72 is bent in the direction in which the cutoff portion 73 is included and the case in which the distal end side winding portion 72 is bent in the direction in which the cutoff portion 73 is not included are compared, the bending characteristic significantly changes, in the coil-shaped member 35A. More specifically, bending to the cutoff portion 73 side can be performed more easily as compared with the bending in the direction in which the cutoff portion 73 is not included.

The distal end side winding portion 72 is the portion which is disposed in a proximal end bending piece of the bending portion 16 from the distal end of the distal end portion 15 which configures the endoscope insertion portion 11.

Subsequently, the surgeon performs the manipulation of inserting the endoscope insertion portion 11 into the biliary tract 111 from the duodenum 110 with the catheter 3 including the coil-shaped member 35A in the catheter insertion portion 31. At this time, the surgeon disposes the distal end side winding portion 72 in the bending portion 16 from the distal end of the endoscope insertion portion 11, and disposes the distal end side winding portion 72 with the orientation in the bending portion 16 taken into consideration so that the cutoff portion 73 is oriented to the biliary tract direction in the duodenum.

Subsequently, the surgeon inserts the distal end portion 15 of the endoscope insertion portion 11 to the vicinity of the biliary tract outlet 112 of the biliary tract 111. Thereafter, the surgeon performs bending operation of the bending operation device 18 provided at the endoscope operation section 12. Thereupon, the bending portion 16 is easily bent because the cutoff portion 73 is provided at the distal end side winding portion 72 of the coil-shaped member 35A. As a result, the front end face of the distal end portion 15 can be smoothly caused to face the biliary tract outlet 112.

As above, the cutoff portion 73 is provided at the distal end side winding portion 72 of the coil-shaped member 35A, and the cutoff portion 73 is disposed to be oriented to the predetermined direction in the treatment instrument channel in the bending portion 16. Thereupon, the surgeon performs bending operation of the bending operation device 18 with a small bending force amount, and can smoothly bend the bending portion 16 in the state in which the coil-shaped member 35A is disposed in the treatment instrument channel.

A cutoff portion which makes a half of the entire circumference of the distal end side winding portion of the coil-shaped member 35 of the above described embodiment in a semicircular shape is formed, and the bending characteristic of the distal end side winding portion of the coil-shaped member 35 may be changed.

Further, the configuration of the coil-shaped member of the catheter insertion portion is not limited to the configuration described above, and the distal end side winding portion 72 of a coil-shaped member 35B may be formed by a coil in which the element wire diameter periodically changes to a small diameter and a large diameter being wound around.

The distal end side winding portion 72A of the coil-shaped member 35B shown in FIG. 13 is configured by the element wire with the element wire diameter periodically changing being wound around. The distal end side winding portion 72A includes a small-diameter wire wound portion 75 which is formed by a small-diameter element wire with the wire diameter being a small diameter in an upper half in the drawing which is a half of the entire circumference, and includes a large-diameter wire wound portion 76 formed by a large-diameter element wire with a wire diameter being larger than the small-diameter element wire by a predetermined dimension in a lower half in the drawing.

According to the configuration, when the case in which the distal end side winding portion 72A of the coil-shaped member 35B is bent to the small-diameter wire wound portion 75 side, and the case in which the distal end side winding portion 72A is bent to the large-diameter wire wound portion 76 side are compared, bending to the small-diameter wire wound portion 75 side is more easily performed as compared with bending to the large-diameter wire wound portion 76 side. As a result, the operation and the effect similar to those of the coil-shaped member 35A described above can be obtained.

The cutoff portion may be disposed in only a range from a position 100 mm from the catheter distal end to 180 mm. According to the configuration, traveling of the catheter is along a shape of an intracorporeal tube cavity, and therefore, stable fixation of the catheter is enabled.

Figure 14:
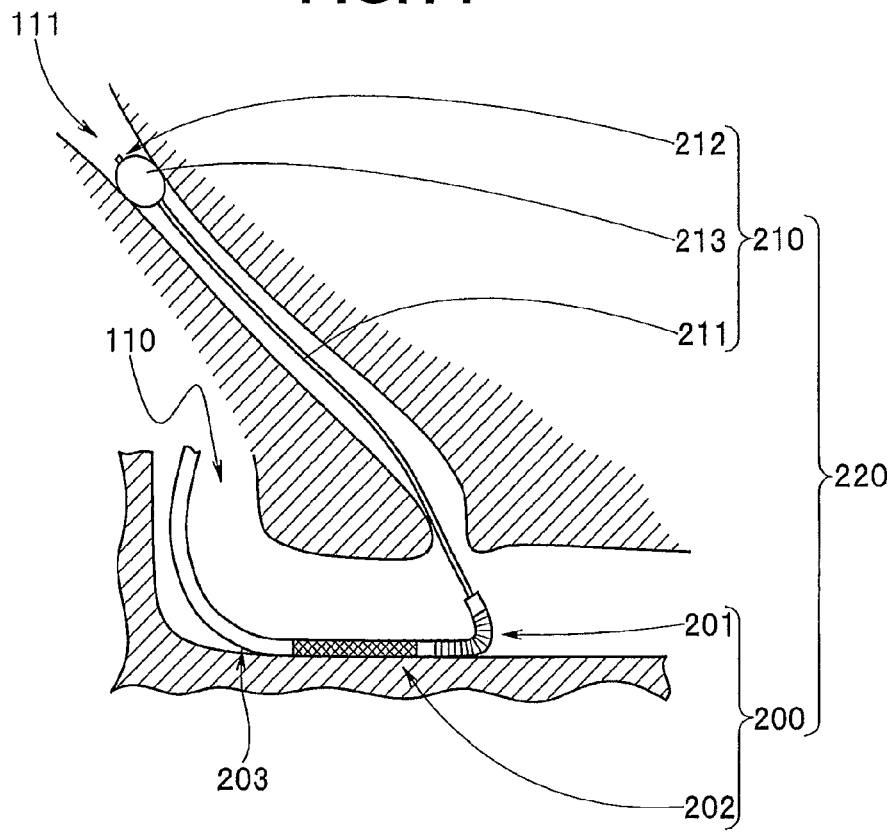
FIG. 14 is a view showing a state in which the balloon of the catheter insertion portion is inflated and is fixed in close contact with a wall of the biliary tract, in order to insert an endoscope insertion portion into the biliary tract, in an endoscope system including an endoscope having a first bending portion and a second bending portion in an endoscope insertion portion, and a catheter with a balloon.

Incidentally, FIG. 14 shows an endoscope system 220 including an endoscope 200 and a catheter 210 with a balloon. The endoscope 200 has a first bending portion 201 and a second bending portion 202 at an endoscope insertion portion 203. A balloon 213 is provided at a distal end portion 212 which configures a catheter insertion portion 211 of the catheter 210 with the balloon. The balloon 213 is in an inflated state and is fixed in close contact with a wall of the biliary tract 111.

Figure 15:
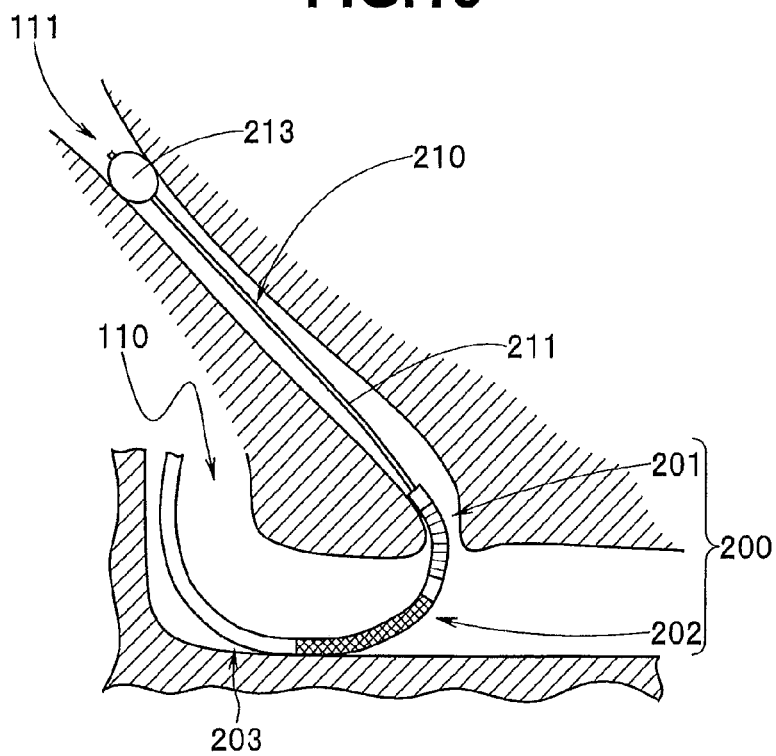
FIG. 15 is a view showing a state in which the first bending portion of the endoscope insertion portion moves along the catheter insertion portion in a stretched state and is inserted and disposed in the biliary tract.

In the state, a surgeon performs an operation of bending the second bending portion 202 included in the endoscope insertion portion 203 of the endoscope 200 and at the same time, by, for example, an assistant, an operation of pulling back the catheter insertion portion 211 of the catheter 210 with the balloon is performed. Thereupon, the catheter insertion portion 211 is changed to a state in which the catheter insertion portion 211 is stretched with a predetermined tension by the pullback operation of the assistant as shown in FIG. 15. Meanwhile, with the bending operation of the second bending portion 202 of the surgeon, the second bending portion 202 bends. Thereupon, the first bending portion 201 in the bending-free state moves along the catheter insertion portion 211 which is changed to the stretched state, and is inserted and disposed in the biliary tract 111.

Figure 16:
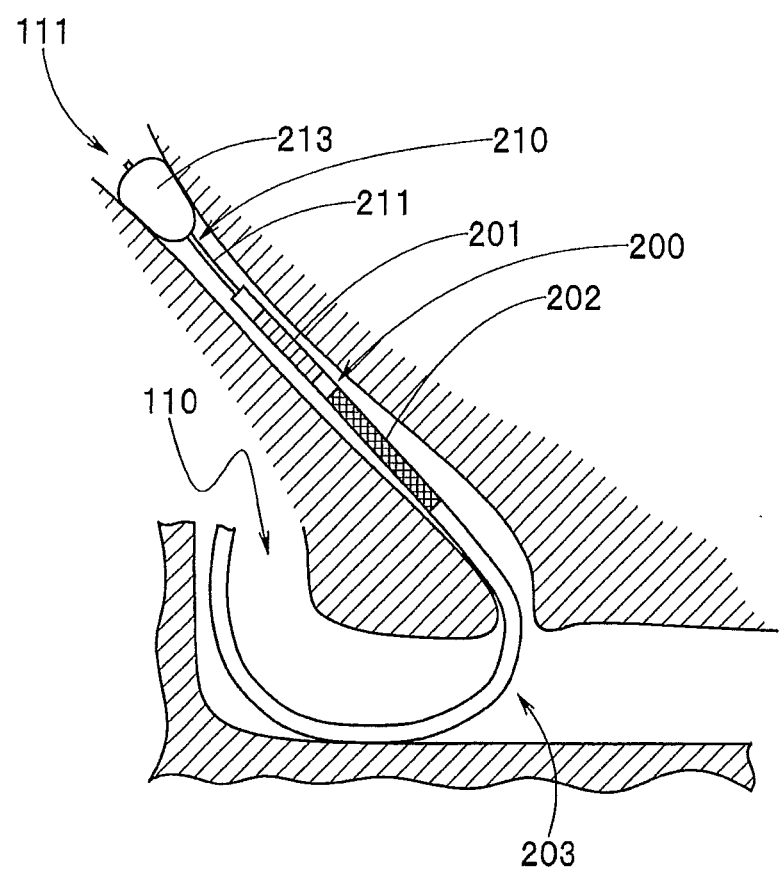
FIG. 16 is a view showing a state in which the first bending portion and the second bending portion in a bending-free state are introduced to a vicinity of the balloon along the catheter insertion portion.

Thereafter, an operation of bringing the catheter insertion portion 211 into a stretched state is performed, and an operation of causing the endoscope insertion portion 203 to advance is performed. Thereupon, the first bending portion 201 and the second bending portion 202 which are in the bending-free state can be introduced to a vicinity of the balloon 213 in the biliary tract along the catheter insertion portion 211, as shown in FIG. 16.

However, in the endoscope system 220 described above, the operation of bending the second bending portion 202 by the surgeon, and the operation of pulling back the catheter insertion portion 211 by the assistant are required. Therefore, in the situation in which the assistant cannot lend a hand, that is, by the surgeon alone, it is difficult to shift to the operation of introducing the endoscope insertion portion 203 into the biliary tract 111 along the catheter insertion portion 211. Therefore, a surgeon desires an endoscope with a second bending portion capable of performing two operations described above by the surgeon alone.

Here, with reference to FIG. 17 to FIG. 26, a configuration of the endoscope with the second bending portion will be described. The endoscope with the second bending portion includes a first bending portion and a second bending portion, and enables a surgeon alone to perform an operation of bending the second bending portion and an operation of pulling back the catheter insertion portion at the same time.

Figure 17:
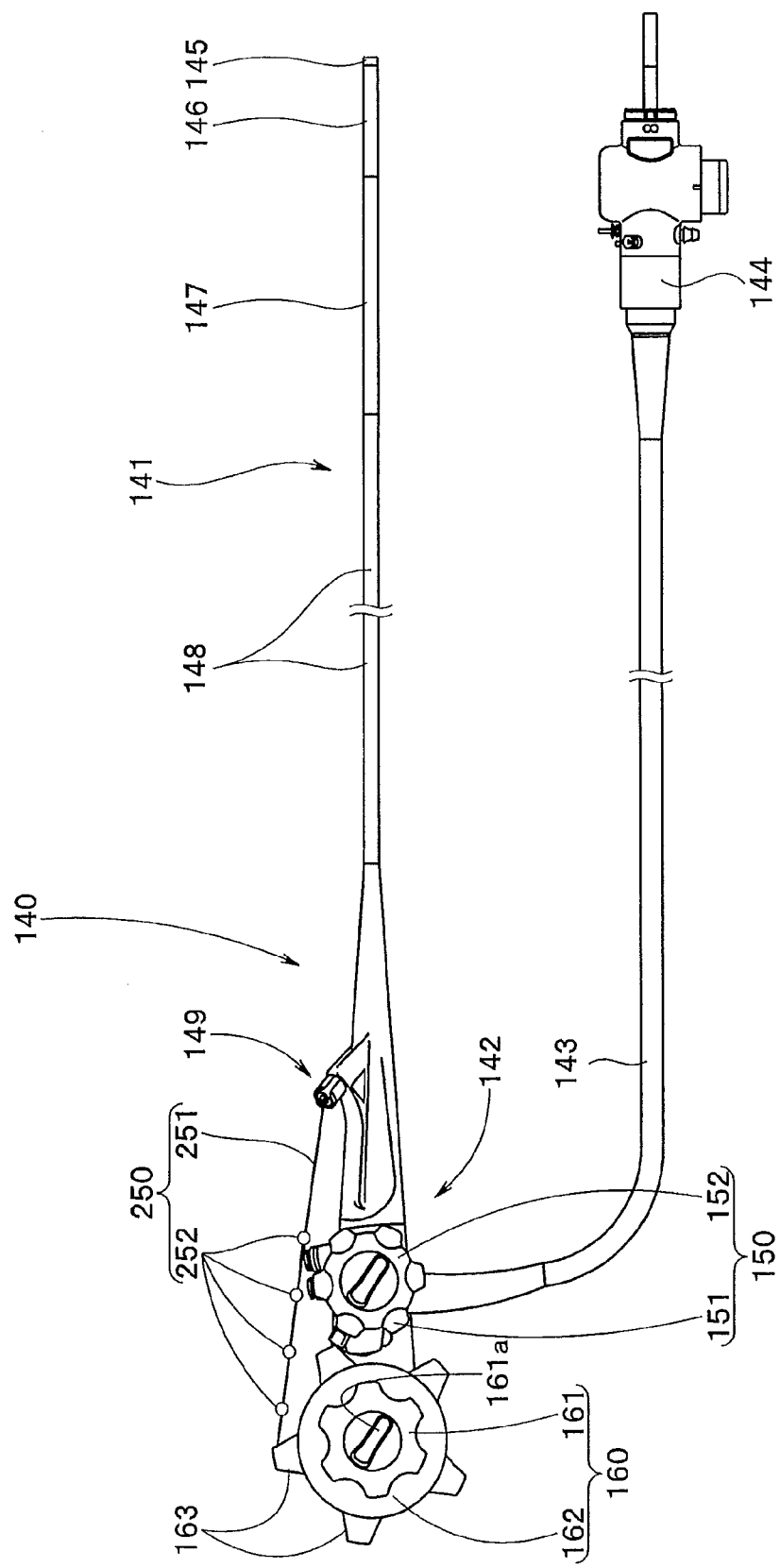
FIG. 17 is a view explaining an endoscope with a second bending portion in which a first operation device and a second operation device are provided at an operation section.

An endoscope 140 with a second bending portion shown in FIG. 17 is configured by including an elongated insertion portion 141, an operation section 142, and a universal cord 143 which is extended from a side portion of the operation section 142. The insertion portion 141 and the universal cord 143 have flexibility. The operation section 142 is provided at a proximal end side of the insertion portion 141. An endoscope connector 144 is provided at an end portion of the universal cord 143. The endoscope connector 144 is detachably connected to, for example, a light source apparatus (not illustrated) which is an outside apparatus.

The insertion portion 141 is configured by connectively providing a distal end portion 145, a first bending portion 146, a second bending portion 147, and a flexible tube portion 148 having flexibility in sequence in order from a distal end side.

The first bending portion 146 is connectively provided at a proximal end side of the distal end portion 145. The second bending portion 147 is connectively provided at a proximal end side of the first bending portion 146. In the present embodiment, the first bending portion 146 includes a bending portion group which is configured to be bendable in, for example, vertical and lateral directions by a plurality of bending pieces being continuously connected. The second bending portion 147 includes a bending portion group which is configured to be bendable in a vertical direction by a plurality of bending pieces being continuously connected.

Reference sign 149 designates a treatment instrument insertion port. A catheter insertion portion 251 of, for example, a catheter 250 with a balloon which is a treatment instrument is inserted through a treatment instrument channel (not illustrated) via the treatment instrument insertion port 149, and is guided into a body.

The catheter insertion portion 251 of the present embodiment includes a plurality of holding portions 252 at an insertion portion proximal end side which is disposed at an outside from the treatment instrument insertion port 149. The holding portion 252 is a projected portion which is protruded from the catheter insertion portion 251. The holding portion 252 is, for example, a spherical portion.

The operation section 142 is provided with a first operation device 150 and a second operation device 160.

The first operation device 150 includes a vertical bending knob 151 and a lateral bending knob 152 for performing bending operation of the first bending portion 146. The second operation device 160 includes a catheter advancing and retracting knob (hereinafter, abbreviated as an advancing and retracting knob) 162 which advances and retracts the vertical bending knob 161 for performing bending operation of the second bending portion 147 and the catheter insertion portion 251.

The vertical bending knob 151 is in, for example, a ring shape, and causes the first bending portion 146 to perform bending operation in the vertical direction with the rotational operation. The lateral bending knob 152 is in a ring shape with a diameter smaller than that of the vertical bending knob 151, for example. The lateral bending knob 152 causes the first bending portion 146 to perform bending operation in the lateral direction with rotational operation. More specifically, the vertical bending knob 151 bends the first bending portion 146 in, for example, an upper direction by being rotated in a counterclockwise direction. Meanwhile, the lateral bending knob 152 bends the first bending portion 146 in, for example, a right direction by being rotated in the counterclockwise direction.

The vertical bending knob 161 is also in, for example, a ring shape, and causes the second bending portion 147 to perform bending operation in the vertical direction. More specifically, the vertical bending knob 161 bends the second bending portion 146 in the upper direction by being rotated in the counterclockwise direction.

The advancing and retracting knob 162 is in a ring shape with a diameter larger than that of the vertical bending knob 161. The advancing and retracting knob 162 advances and retracts the catheter insertion portion 251 with a rotational operation. The advancing and retracting knob 162 includes a plurality of protruded portions 163 which are protruded from an outer circumferential face. Five of the protruded portions 163 are provided on, for example, an outer circumference, and are disposed equidistantly with respect to a circumferential direction.

The number of the protruded portions 163 is not limited to five, and may be smaller than five or larger than five.

Figure 18:
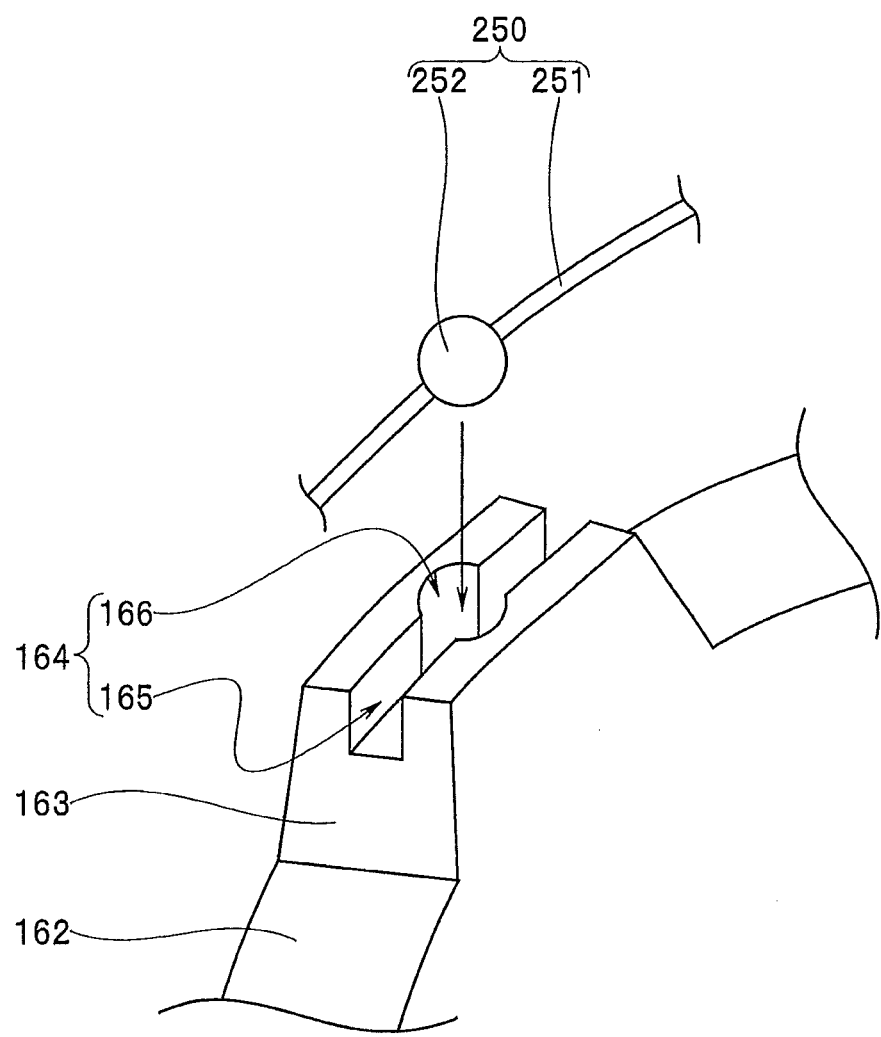
FIG. 18 is a view explaining a configuration and an operation of a protruded portion which a catheter advancing and retracting knob includes.

As shown in FIG. 18, the protruded portion 163 has a catheter insertion portion holding portion 164. The catheter insertion portion holding portion 164 is configured by including an insertion portion disposition groove 165, and a holding hole 166. The insertion portion disposition groove 165 is a groove elongated in the circumferential direction. The holding hole 166 is formed in a center of the groove 165. The holding portion 252 is disposed in the holding hole 166. The catheter insertion portion 251 is disposed in the insertion portion disposition groove 165.

A space between the holding portions 252 included in the catheter insertion portion 251 corresponds to a space between the holding holes 166 provided in the adjacent protruded portions 163 which are formed at the advancing and retracting knob 162.

According to the configuration, in a state in which the holding portion 252 is disposed in the holding hole 166 of the protruded portion 163, the advancing and retracting knob 162 is rotated in the counterclockwise direction, whereby the catheter insertion portion 251 is towed. Subsequently, the advancing and retracting knob 162 is successively rotated in the counterclockwise direction, whereby the holding portion 252 which is located at the treatment instrument insertion port 149 side is disposed in the holding hole 166 of the adjacent protruded portion 163 and the catheter insertion portion 251 is further towed.

Figure 19:
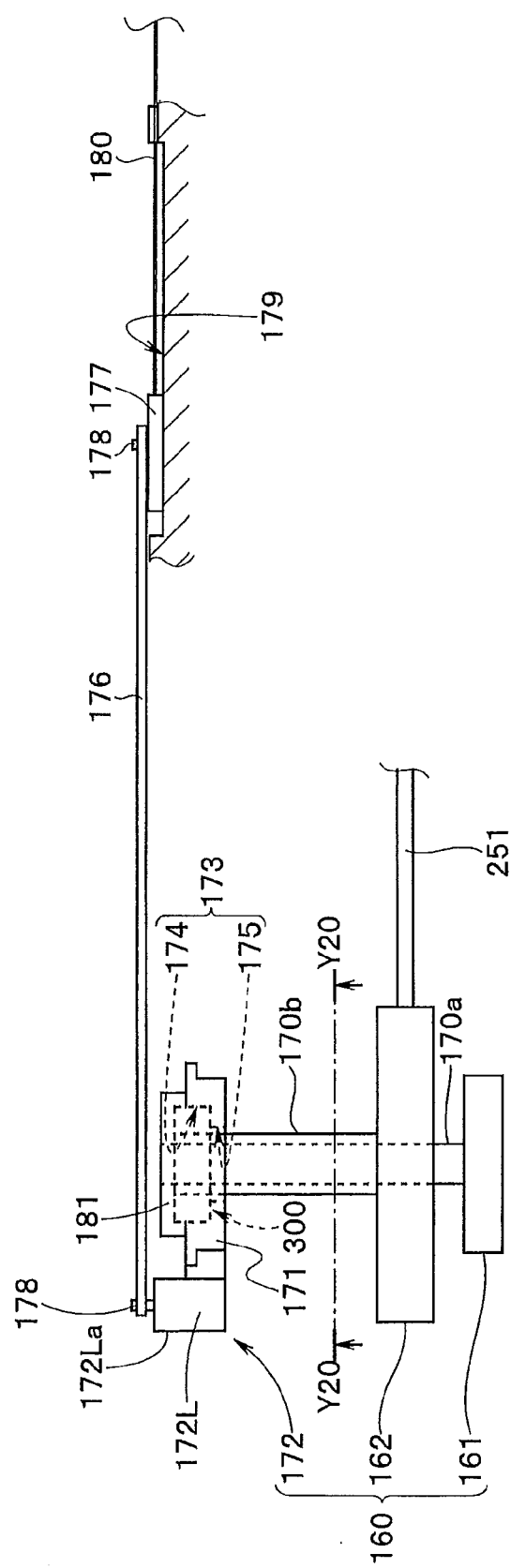
FIG. 19 is a plan view explaining the second operation device including a selective power transmitting mechanism portion.

As shown in FIG. 19, the second operation device 160 is configured by including the vertical bending knob 161, the advancing and retracting knob 162, and a direct-acting link mechanism 172. Reference sign 300 designates an independent/accompanying rotation mechanism portion which configures a selective power transmitting mechanism portion, which will be described later.

The vertical bending knob 161 is fixed to a first knob shaft 170a. The advancing and retracting knob 162 is fixed to a second knob shaft 170b. In the present embodiment, the second knob shaft 170b is a pipe-shaped member. The first knob shaft 170a is a columnar member. The first knob shaft 170a is pivotally disposed in a through-hole which the second knob shaft 170b has. A distal end side of the first knob shaft 170a is configured to be protruded by a predetermined amount from a distal end of the second knob shaft 170b.

To a predetermined position at the distal end side of the first knob shaft 170a, a ring-shaped member 171 having a through-hole 173 is fixed via an integral fastening member not illustrated, or the first knob shaft 170a is directly fixed to a communication hole (reference sign 312), which will be described later.

The through-hole 173 is in a stepped shape having a recessed portion 174 and a communication hole 175. The independent/accompanying rotation mechanism portion 300 is placed in the recessed portion 174. The communication hole 175 allows the recessed portion 174 and the outside to communicate with each other.

Figure 20:
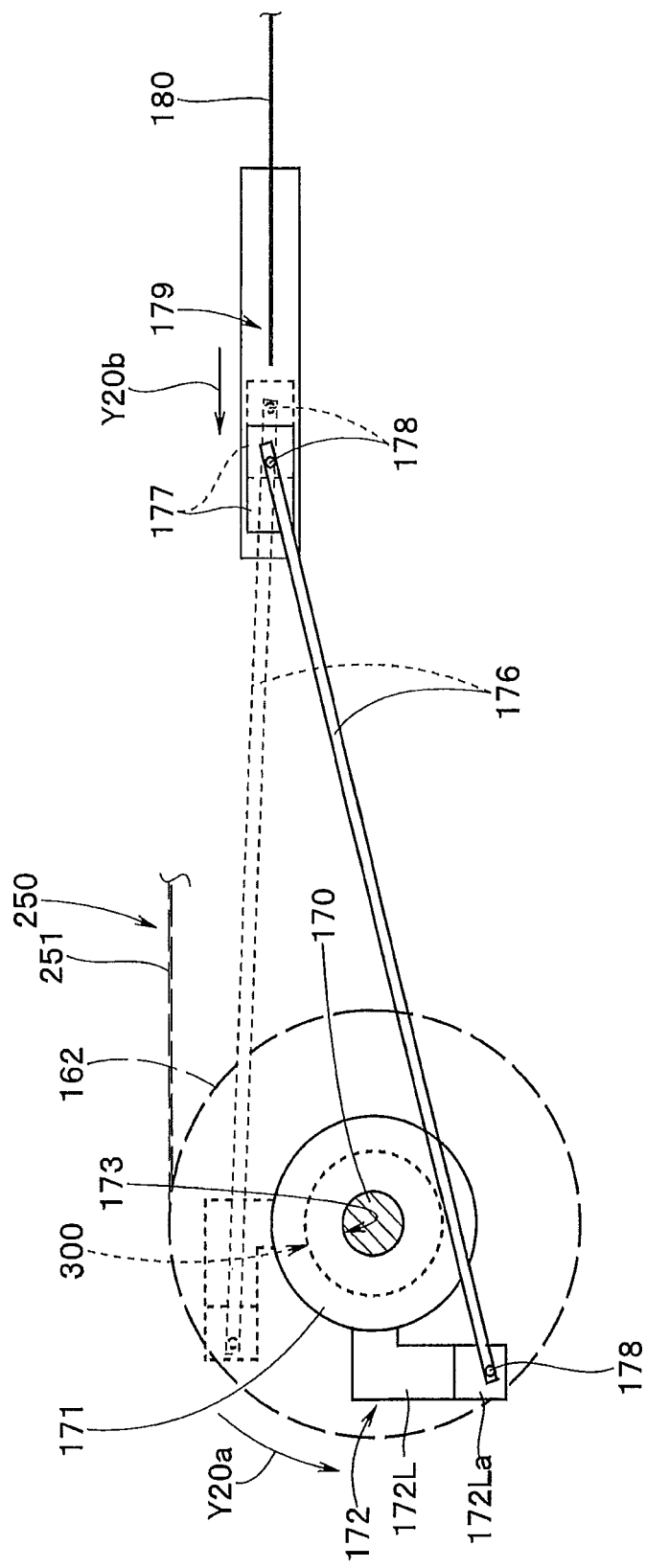
FIG. 20 is a side view explaining the second operation device including the selective power transmitting mechanism portion.

As shown in FIG. 19 and FIG. 20, the ring-shaped member 171 is provided with a protruded portion 172L which configures the direct-acting link mechanism 172. The protruded portion 172L is provided at a predetermined position with respect to the ring-shaped member 171.

In FIG. 20, the advancing and retracting knob 162 and the catheter insertion portion 251 which are not illustrated because the advancing and retracting knob 162 and the catheter insertion portion 251 are located at a rear from the line of the arrows Y20 to Y20 of FIG. 19, are shown by the broken lines.

Further, the ring-shaped member 171 and the protruded portion 172L may be of an integral structure or may be of a separate structure. When the ring-shaped member 171 and the protruded portion 172L are separate bodies, the ring-shaped member 171 and the protruded portion 172L are integrally configured by screwing by a screw member, adhesion, welding or the like.

The direct-acting link mechanism 172 is mainly configured by including the protruded portion 172L, a drive force transmitting rod 176, a slide member 177 and a pair of connection pins 178. The protruded portion 172L includes a projected portion 172La. At the projected portion 172La, the connection pin 178 is protrudingly provided. One end portion of the drive force transmitting rod 176 is pivotally connected to the connection pin 178.

The slide member 177 is slidably disposed in a slide groove 179 provided in the operation section 142. The connection pin 178 is also protrudingly provided at one surface side of the slide member 177. The other end portion of the drive force transmitting rod 176 is pivotally connected to the connection pin 178.

A proximal end portion of an upper direction towing wire 180 for the second bending portion (hereinafter, abbreviated as a wire for the second bending portion) is fixed to a distal end side end portion of the slide member 177. The other end portion of the wire 180 for the second bending portion is fixedly provided at a predetermined position of a distal end bending piece which configures the bending portion group, not illustrated, of the second bending portion 147.

In the present embodiment, the slide member 177 which configures the direct-acting link mechanism 172 is moved to a left end side shown by the solid line in the drawing of the slide groove 179, whereby the second bending portion 147 is brought into a maximum bent state with respect to the upper direction.

More specifically, when the protruded portion 172L rotates in the counterclockwise direction as shown by the arrow Y20a from the position shown by the broken line with rotation of the ring-shaped member 171, the drive force transmitting rod 176 which is connected to the projected portion 172La of the protruded portion 172L moves the slide member 177 located in the slide groove 179 to the direction of the arrow 20b from the position shown by the broken line. As a result, the wire 180 for the second bending portion which is fixed to the slide member 177 is towed, and the second bending portion 147 performs bending operation in the upper direction.

The vertical bending knob 161 is configured to be fixable to a desired rotation position by a dial (see reference sign 161a of FIG. 17). Further, the second bending portion 147 of the present embodiment is configured to be bent in only one direction in the upper direction by operation of the vertical bending knob 161.

Here, the independent/accompanying rotation mechanism portion 300 will be described.

Figure 21:
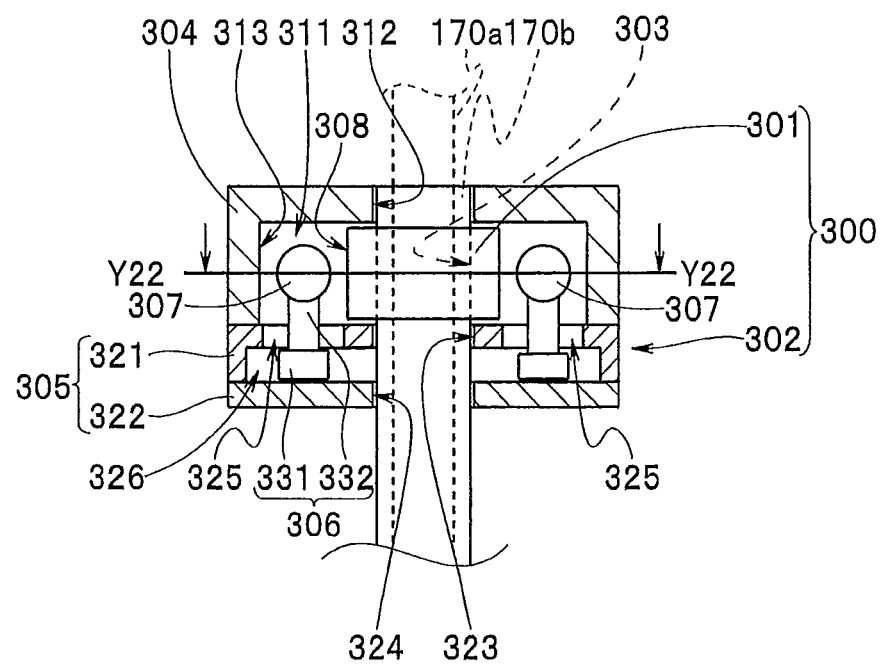
FIG. 21 is a sectional view in a knob axis longitudinal direction explaining a configuration of an independent/accompanying rotation mechanism portion.
Figure 22:
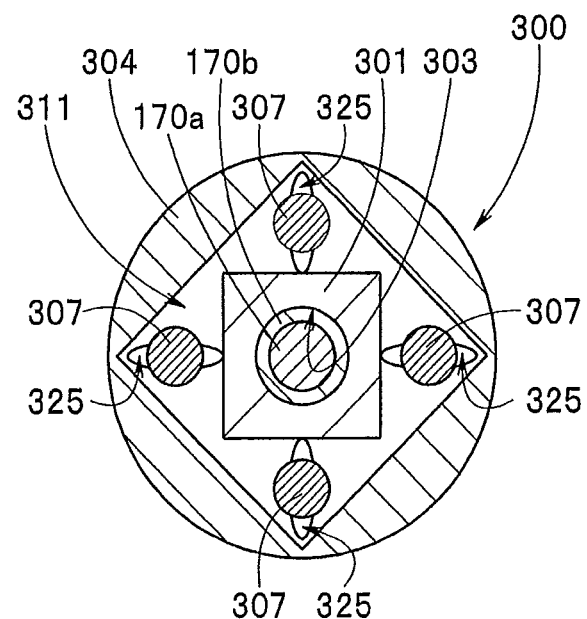
FIG. 22 is a sectional view taken along the line of the arrows Y22 to Y22 of FIG. 21.

As shown in FIG. 21 and FIG. 22, the independent/accompanying rotation mechanism portion 300 is configured by including a first rotation body 301 and a rotational force transmission switching portion 302.

The first rotation body 301 is a rectangular parallelepiped with a cross-sectional shape of an equilateral rectangle, and includes a central through-hole 303. The second knob shaft 170b is inserted through an inside of the central through-hole 303. The first rotation body 301 is integrally fixed to a predetermined position of a longitudinal axis of the second knob shaft 170b by, for example, a screw member.

The rotational force transmission switching portion 302 is configured by including a second rotation body 304, a case body 305, a moving member 306 and sphere portions 307.

The second rotation body 304 is a cylindrical member. The second rotation body 304 is integrally fixed to the recessed portion 174 which configures the through-hole 173 of the ring-shaped member 171 by screwing by the screw member, adhesion, welding or the like.

In the second rotation body 304, a recessed portion 311 for disposing the first rotation body (hereinafter, abbreviated as a disposition recessed portion), and a communication hole 312 are formed. The disposition recessed portion 311 has a cross-sectional shape of, for example, an equilateral rectangle. The communication hole 312 allows the disposition recessed portion 311 and the outside to communicate with each other.

In the disposition recessed portion 311, the first rotation body 301 is rotatably disposed. In the communication hole 312, a distal end portion of the second knob shaft 170b, for example, is pivotally disposed. The configuration in which only the first knob shaft 170a passes in the communication hole 312 may be adopted.

The case body 305 is of, for example, a two-body structure, and is configured by a case main body 321 and a lid body 322. The case main body 321 has, for example, a recessed portion. The case main body 321 is integrally fixed to the second rotation body 304 by screwing by a screw member, adhesion, welding or the like. The lid body 322 is integrally fixed to the case main body 321 by screwing by a screw member, adhesion, welding or the like.

In the case main body 321, a through-hole 323 through which the second knob shaft 170b is pivotally inserted is formed. In the case main body 321, long holes 325 which are plural elongated through-holes are formed in a center axis direction of the through-hole 323 from outside of the case main body. As the plurality of long holes 325, four of the long holes are formed at the intervals of 90 degrees in a circumferential direction around the center axis of the through-hole 323 to conform to a sectional shape of the disposition recessed portion 311. In the lid body 322, a through-hole 324 through which the second knob shaft 170b is pivotally inserted is formed.

The moving member 306 is a stepped columnar member with a sectional shape of a substantially T-shape. The moving member 306 is configured by including, for example, a large diameter portion 331 and a small diameter portion 332. The large diameter portion 331 is a slide portion which is slidably disposed in a space portion 326 which is configured by the case main body 321 and the lid body 322. In contrast with this, the small diameter portion 332 is disposed in the disposition recessed portion 311 by passing through the long hole 325.

The large diameter portion 331 is slidable in the space portion 326, and the small diameter portion 332 is slidable with respect to the long hole 325. More specifically, the moving member 306 is movable along the long hole 325.

The sphere portion 307 is fixedly provided at a distal end portion of the small diameter portion 332 of the moving member 306. A diameter of the sphere portion 307 is set to a predetermined dimension. More specifically, the diameter of the sphere portion 307 is set with a gap between an inner side surface 313 of the disposition recessed portion 311 and an outer side surface 308 of the first rotation body 301 which are disposed to be opposed to each other as a reference.

Figure 23:
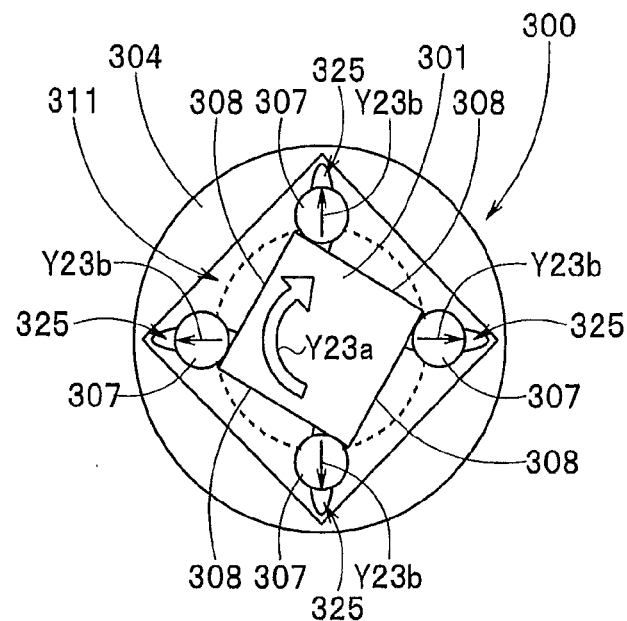
FIG. 23 is a view explaining a state in which an outer side surface of a first rotation body which is rotating, contacts a sphere portion when the first rotation body of the independent/accompanying rotation mechanism portion is rotated.

In the independent/accompanying rotation mechanism portion 300, when the first rotation body 301 is rotated clockwise as shown by the arrow Y23a as shown in FIG. 23, the outer side surface 308 of the first rotation body 301 contacts the sphere portions 307. Thereafter, the first rotation body 301 is further rotated clockwise, whereby the sphere portions 307 move along the long holes 325 as shown by the arrow Y23b.

Figure 24:
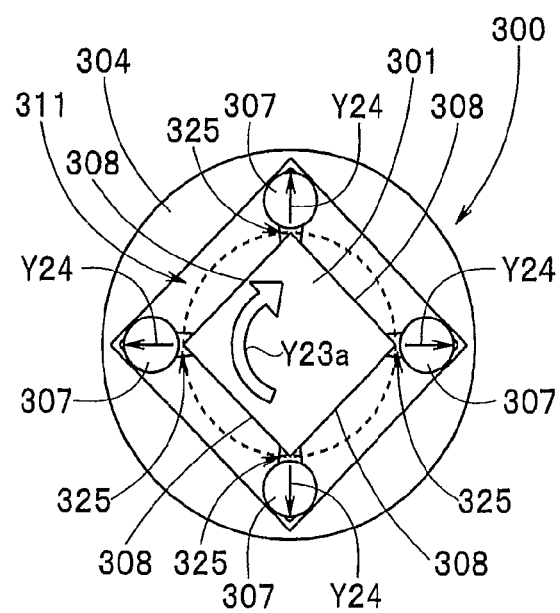
FIG. 24 is a view explaining rotation of the first rotation body.

Subsequently, the first rotation body 301 is further rotated in the same direction, whereby the sphere portions 307 are moved to corner portions of the disposition recessed portion 311 as shown by the arrow Y24 of FIG. 24. As a result, the first rotation body 301 individually rotates clockwise without being hindered from rotating by the sphere portions 307.

When the first rotation body 301 is rotated in the counterclockwise direction, the first rotation body 301 individually rotates counterclockwise. The circles by the broken lines shown in FIGS. 23 and 24 are movement trajectories of the corners of the first rotation body 301. Further, the configuration in which the recessed portion configuring the space portion 226 is provided in the case main body 321 is adopted, but the recessed portion may be provided by the space portion 326 being configured in the lid body 322.

Figure 25:
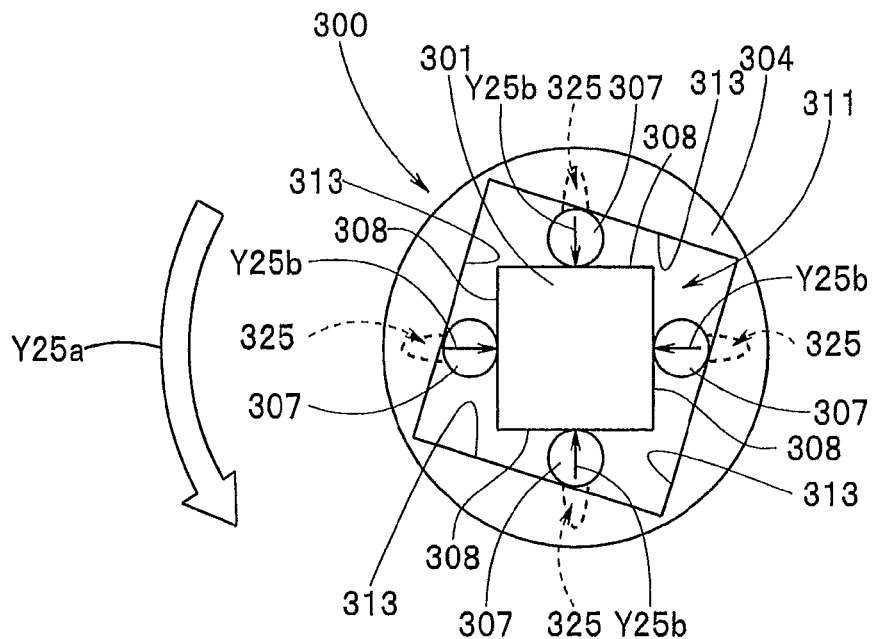
FIG. 25 is a view explaining a state in which an inner side surface of a second rotation body which is rotating, contacts the sphere portion when the second rotation body of the independent/accompanying rotation mechanism portion is rotated.

Meanwhile, in the independent/accompanying rotation mechanism portion 300, when the second rotation body 304 is rotated counterclockwise as shown by the arrow 25a as shown in FIG. 25, the inner side surface 313 contacts the sphere portion 307. Thereafter, the second rotation body 304 is further rotated counterclockwise, whereby the sphere portion 307 moves toward the outer side surface 308 along the long hole 325 to contact the outer side surface 308 as shown by Y25b.

Figure 26:
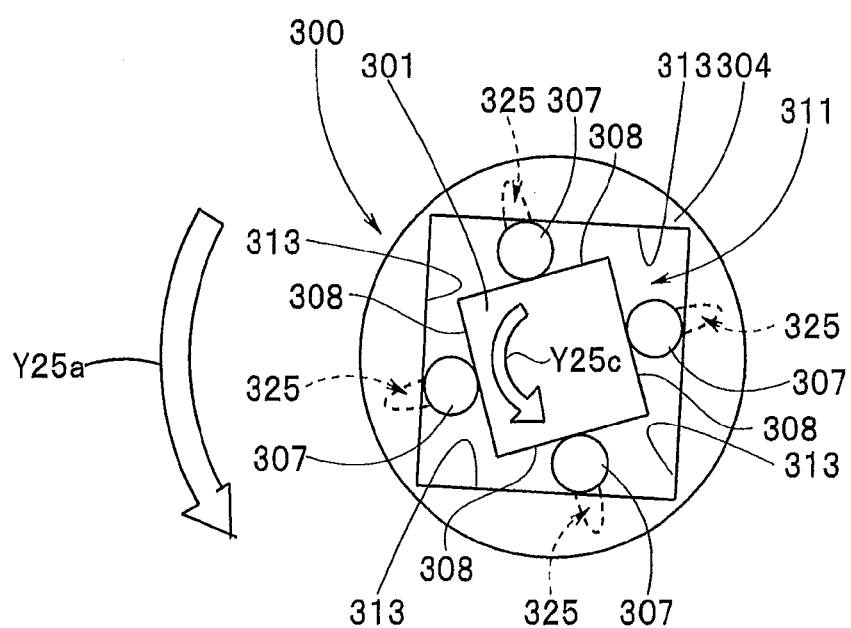
FIG. 26 is a view explaining an accompanying rotation state in which the first rotation body rotates by accompanying rotation of the second rotation body.

After the contact, the second rotation body 304 is further rotated in the same direction, the sphere portions 307 are held in the state in which the sphere portions 307 are sandwiched by the inner side surface 313 and the outer side surface 308 as shown in FIG. 26. More specifically, the second rotation body 304 and the first rotation body 301 become integral by interposing the sphere portions 307 therebetween.

As a result, the rotational drive force of the second rotation body 304 is transmitted to the first rotation body 301 via the sphere portions 307. Thereupon, the first rotation body 301 also rotates counterclockwise as shown by the arrow 25c with counterclockwise rotation shown by the arrow 25a of the second rotation body 304. More specifically, the first rotation body 301 is rotated in the same direction with the rotation of the second rotation body 304.

The first rotation body 301 of the independent/accompanying rotation mechanism portion 300 configured as described above is integrally fixed to the second knob shaft 170b of the advancing and retracting knob 162. Meanwhile, the second rotation body 304 of the independent/accompanying rotation mechanism portion 300 is integrally fixed to the first knob shaft 170a of the vertical bending knob 161 via the ring-shaped member 171 and the integrally fastening member 181.

As a result, when the advancing and retracting knob 162 is rotationally operated in the clockwise direction or in the counterclockwise direction of FIG. 17, for example, by the surgeon, the second knob shaft 170b and the first rotation body 301 rotate in the clockwise direction or in the counterclockwise direction with rotation of the advancing and retracting knob 162. As a result, the catheter insertion portion 251 individually moves to advance and retract as described above.

Meanwhile, when the vertical bending knob 161 is operated in the counterclockwise direction in FIG. 17 by the surgeon, the ring-shaped member 171 integral with the first knob shaft 170a is rotated in the counterclockwise direction. In addition, the second rotation body 304 which is integral with the recessed portion 174 of the ring-shaped member 171 rotates in the counterclockwise direction, and the protruded portion 172L integral with the direct-acting link mechanism 172 rotates in the counterclockwise direction. Thereupon, as shown in FIG. 26 described above, the first rotation body 301 rotates in the same direction with the rotation of the second rotation body 304, and the second bending portion 147 performs bending motion in the upper direction, while the advancing and retracting knob 162 is rotated in the counterclockwise direction, and the catheter insertion portion 251 is towed.

More specifically, the independent/accompanying rotation mechanism portion 300 is provided at the second operation device 160 which configures the endoscope 140 with the second bending portion of the present embodiment. As a result, the surgeon can selectively perform the operation of individually advancing and retracting only the catheter insertion portion 251 by selecting the operation of the advancing and retracting knob 162, and the accompanying operation of towing the catheter insertion portion 251 with the upper direction bending operation of the second bending portion 147 by selecting the operation of the vertical bending knob 161.

The cross-sectional shape of the first rotation body 301 is set as an equilateral rectangle, but the cross-sectional shape is not limited to the equilateral rectangle, but may be an equilateral triangle, an equilateral hexagon, an equilateral octagon and the like. The cross-sectional shape of the disposition recessed portion 311 in which the first rotation body 301 is disposed is not limited to an equilateral rectangle, either, and is configured to correspond to the shape of the first rotation body 301.

Further, in the present embodiment, the advancing and retracting knob 162 is rotated in the counterclockwise direction with the rotation operation in the counterclockwise direction of the vertical bending knob 161. However, the position of the protruded portion 172L which is provided at the ring-shaped member 171 is changed, and the configuration which rotates the advancing and retracting knob 162 in the clockwise direction with rotation operation in the counterclockwise direction of the vertical bending knob 161, or the configuration of rotating the advancing and retracting knob 162 in the clockwise direction, or in the counterclockwise direction with rotation operation in the clockwise direction of the vertical bending knob 161 may be adopted.

An operation of the endoscope 140 with the second bending portion configured as described above will be described.

In the endoscope 140 with the second bending of the present embodiment, the surgeon first brings the balloon 213 which is provided at the distal end portion 212 of the catheter insertion portion 211 of the catheter 210 with the balloon which is led out from the endoscope 140 into the inflated state as shown in the aforementioned FIG. 14 and fixes the balloon 213 in close contact with the wall of the biliary tract 111. After the state is brought about, the surgeon performs an operation of rotating the vertical bending knob 161 in the counterclockwise direction. Thereupon, the second bending portion 147 of the endoscope 140 with the second bending bends in the upper direction, and the catheter insertion portion 211 of the catheter 210 with the balloon is pulled back. As a result, the first bending portion 146 in the bending-free state moves along the catheter insertion portion 211 which is changed into the stretched state. As a result, the distal end portion 145 and the distal end side of the first bending portion 146 are inserted and disposed in the biliary tract 111 as shown in the aforementioned FIG. 15.

As above, the operation section 142 of the endoscope 140 with the second bending portion which includes the first bending portion 146 and the second bending portion 147 is provided with the first operation device 150 which performs bending operation of the first bending portion 146, and the second operation device 160 which performs bending operation of the second bending portion 147 and advances and retracts the catheter insertion portion 251 of the catheter 250 with the balloon. The second operation device 160 is provided with the independent/accompanying rotation mechanism portion 300 which tows the catheter insertion portion 251 which is located outside the treatment instrument insertion port 149 in association with the bending operation of the second bending portion 147.

When the surgeon performs the operation of rotating the vertical bending knob 161 in the counterclockwise direction, the surgeon can perform two operations, that is, the operation of bending the second bending portion 147 in the upper direction, and the operation of bringing the catheter insertion portion 251 into the stretched state at the same time. As a result, the first bending portion 146 is disposed in the biliary tract 111 along the catheter insertion portion 211 which is changed in the stretched state with bending of the second bending portion 147.

Figure 27:
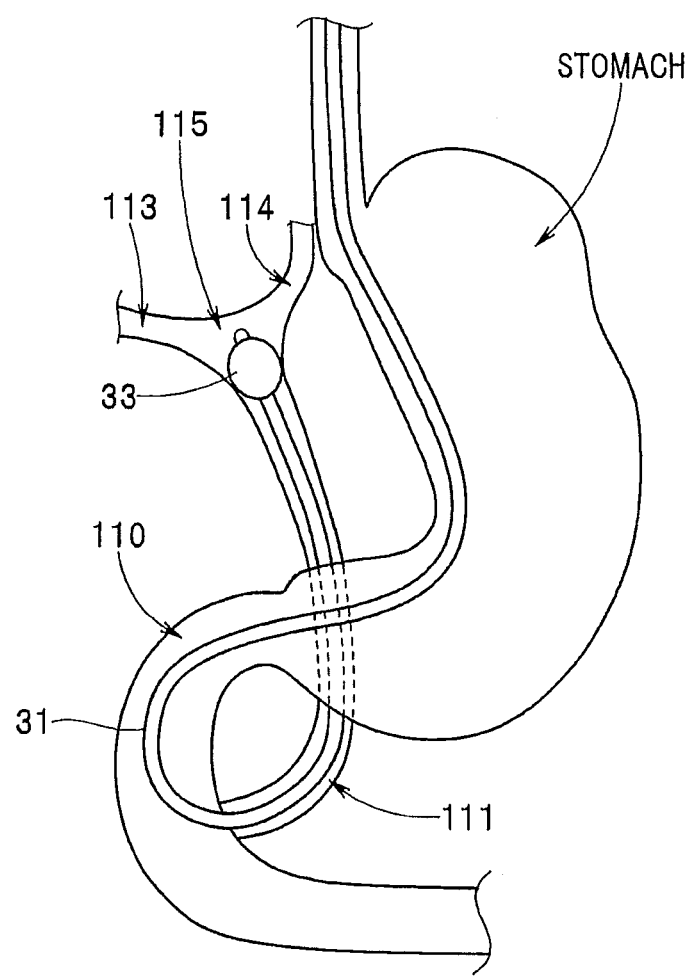
FIG. 27 is a view explaining a balloon which is disposed in a branch portion branching into a gallbladder duct and a common hepatic duct.

In the embodiment described above, the balloon 33 which is provided at the catheter insertion portion 31 is inflated, and is fixed and disposed in close contact with the wall of the biliary tract 111. However, it is conceivable to dispose the balloon 33 in a left and right hepatic ducts confluence portion 115 which is branched to a right hepatic duct 113 and a left hepatic duct 114, which is a part of the biliary tract 111, as shown in FIG. 27. The left and right hepatic ducts confluence portion 115 is a space especially having an expanse. Therefore, when the balloon 33 located in the left and right hepatic ducts confluence portion 115 is inflated, and the balloon 33 is brought into close contact with the wall of the left and right hepatic ducts confluence portion 115, a sufficient close contacting force is unlikely to be obtained.

Therefore, a balloon which can be stably disposed even in the left and right hepatic ducts confluence portion 115 is demanded.

Figure 28A:
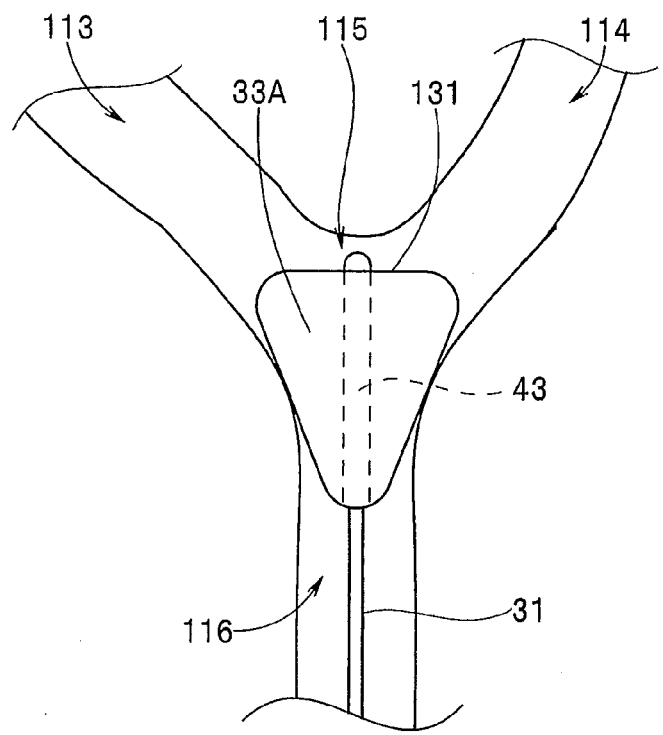
FIG. 28A is a view showing one example of a balloon suitable for being disposed in the branch portion.

A balloon 33A shown in FIG. 28A is in a pipe shape having a large-diameter balloon front end face 131 at a distal end side. The balloon front end face 131 is configured so that a thickness thereof is set to be large as compared with a thickness of other sites of the balloon 33A. Therefore, when air is supplied into the balloon 33A via the fluid tube from the fluid supply and discharge apparatus as described above, a periphery of the balloon front end face 131 is inflated before the balloon front end face 131 is inflated.

As a result, the balloon 33A is inflated into a conical shape in which the distal end side has a large diameter, and the diameter becomes gradually smaller toward a user's hand side. More specifically, the balloon 33A is inflated into the conical shape in the state in which the balloon front end face 131 is disposed in the left and right hepatic ducts confluence portion 115, whereby a side circumferential face of the balloon 33A is caught by a wall of the left and right hepatic ducts confluence portion 115. Thereby, the inflated balloon 33A is stably held and disposed without falling into a common bile duct 116 from the left and right hepatic ducts confluence portion 115.

As above, the inflated shape of the balloon 33A is set to be the conical shape in which the distal end side has a large diameter and the user's hand side has a small diameter, whereby the inflated balloon 33A can be reliably disposed without falling into the common hepatic duct 116. Accordingly, the catheter insertion portion 31 is disposed in the biliary tract 111 in the stable state.

In the state in which the balloon 33A is disposed in the portion other than the left and right hepatic ducts confluence portion 115, the side circumferential face of the balloon 33A is in close contact with the wall of the biliary tract 111 to fix and dispose the catheter insertion portion 31 into the biliary tract 111.

Figure 28B:
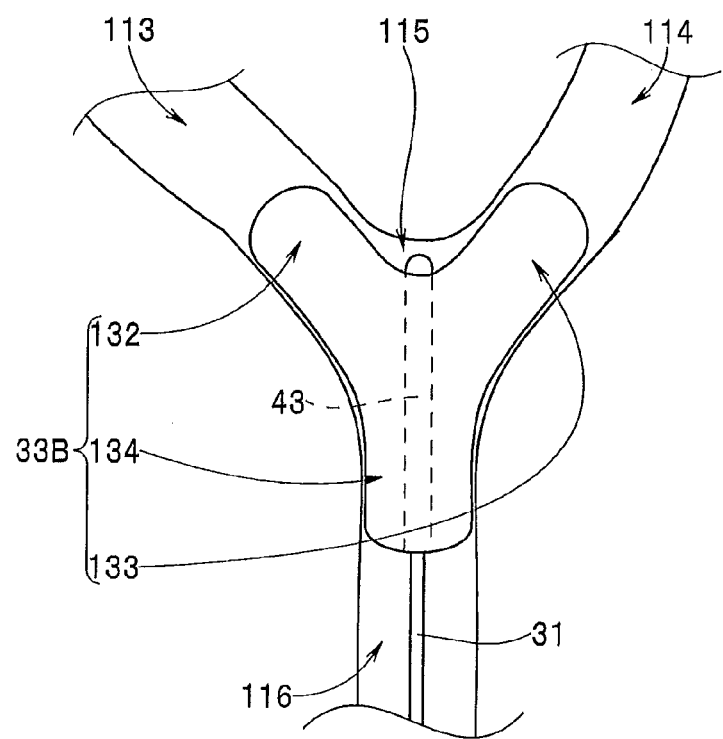
FIG. 28B is a view showing another example of the balloon suitable for being disposed in the branch portion.

The shape at the time of inflation of the balloon is not limited to the conical shape in which the distal end side has a large diameter and the user's hand side has a small diameter, and may be that of a balloon 33B which is inflated into a Y-shape as shown in FIG. 28B.

The balloon 33B is formed into the substantially Y-shape by including a right hepatic duct disposition balloon portion 132 and a left hepatic duct disposition balloon portion 133 which are located at distal end sides, and a common hepatic duct disposition balloon portion 134 which is located at a user's hand side. When air is supplied into the balloon 33B via the fluid tube from the fluid supply and discharge apparatus as described above, the right hepatic duct disposition balloon portion 132 located at the distal end side is inflated in the right hepatic duct 113 as shown in FIG. 28B, and the left hepatic duct disposition balloon portion 133 is inflated in the left hepatic duct 114, while the common hepatic duct disposition balloon portion 134 is inflated in the common hepatic duct 116. The balloon 33B is inflated into the Y-shape.

As a result, a side face of the right hepatic duct disposition balloon portion 132 and the side face of the left hepatic duct disposition balloon portion 133 which configure the balloon 33B are caught by the wall of the left and right hepatic ducts confluence portion 115. Thereby, the inflated balloon 33B is stably held and disposed without falling into the common hepatic duct 116 from the left and right hepatic ducts confluence portion 115.

In a state in which the balloon 33B is disposed at a portion other than the left and right hepatic ducts confluence portion 115, the side face of the right hepatic duct disposition balloon portion 132, the side face of the left hepatic duct disposition balloon portion 133 and the side face of the common hepatic duct disposition balloon portion 134 which configure the balloon 33B are brought into close contact with the wall of the biliary tract 111, and the catheter insertion portion 31 is fixed into the biliary tract 111.

The present invention is not limited only to the embodiment described above, and can be carried out by being variously modified within the range without departing from the gist of the invention.

What is claimed is:

1. An insertion portion rigidity changeable catheter, comprising:
  a catheter insertion portion that includes a sheath main body having a distal end portion and a proximal portion, a longitudinal axis of the catheter insertion portion being defined in a direction connecting the distal end portion and the proximal portion;

a slide member having a distal and a proximal end, the slide member being provided at a proximal end side of the sheath main body to be movable in a direction of the longitudinal axis;

a grasping portion provided at the slide member, the slide member moving in the direction of the longitudinal axis in accordance with an operation of the grasping portion;

a mechanism provided on the sheath main body, the mechanism being in contact with a distal end side of the slide member so as to be operable with the slide member, wherein the slide member is slid and moved in the direction of the longitudinal axis, and a rigidity of the catheter insertion portion is changed in accordance therewith; and an operation section main body for grasping by an operator, the operation section main body being provided at the proximal end side of the sheath main body, wherein the operation section main body comprises:

a sheath fixing member having a cylindrical portion connected with a proximal end of the sheath main body and a plurality of projected portions protruded from an outer circumferential face of the cylindrical portion;

an operation section exterior body having an inner circumferential face in contact with the sheath fixing member; and the slide member comprises a cylinder portion having an inner hole which slides in the direction along the longitudinal axis of the sheath main body; and notches that communicate with the inner hole and an outer circumferential face of the cylinder portion radially and provided at portions corresponding to the projected portions.

2. The insertion portion rigidity changeable catheter according to claim 1, wherein the grasping portion is provided at a proximal side of the slide member with respect to the projected portions.

* * * * *